United States Patent [19]
David et al.

[11] Patent Number: 6,040,303
[45] Date of Patent: Mar. 21, 2000

[54] 7-PHENYL-1, 4-DIAZEPANE COMPOUNDS, PROCESS FOR THEIR PREPARATION, AND PHARMACEUTICAL COMPOSITIONS CONTAINING THEM

[75] Inventors: Samuel David, Hannover; Jochen Antel, Bad Muender; Reinhard Brueckner, Hannover; Dieter Ziegler, Hemmingen; Christian Eeckhout, Lindwedel, all of Germany; Gerhard-Wilhelm Bielenberg, Alfeld, Belgium; Michael Peck, Braine le Chateau, Belgium

[73] Assignee: Solvay Pharmaceuticals GmbH, Hannover, Germany

[21] Appl. No.: 09/141,312

[22] Filed: Aug. 27, 1998

[30] Foreign Application Priority Data

Aug. 27, 1997 [DE] Germany .......................... 197 37 334

[51] Int. Cl.[7] .......................... A61K 31/55; C07D 243/08
[52] U.S. Cl. .......................... 514/218; 540/575
[58] Field of Search ............... 514/218; 540/575

[56] References Cited

U.S. PATENT DOCUMENTS

| | | | |
|---|---|---|---|
| 4,829,061 | 5/1989 | Wolf et al. | 514/218 |
| 5,670,505 | 9/1997 | Matsuo et al. | 514/253 |
| 5,719,156 | 2/1998 | Shue et al. | 514/255 |
| 5,795,894 | 8/1998 | Shue et al. | 514/253 |
| 5,798,359 | 8/1998 | Shue et al. | 514/255 |

FOREIGN PATENT DOCUMENTS

| | | |
|---|---|---|
| 655442 | 5/1995 | European Pat. Off. . |
| 23 28 870 | 1/1975 | Germany . |

OTHER PUBLICATIONS

Patent Abstracts of Japan, vol. 95, No. 9, Oct. 31, 1995. (Abstract of JP 7–145060).
Patent Abstracts of Japan, vol. 18, No. 482, Sep. 8, 1994. (Abstract of JP 6–157442).

*Primary Examiner*—Mukund J. Shah
*Assistant Examiner*—Brenda Coleman
*Attorney, Agent, or Firm*—Evenson, McKeown, Edwards & Lenahan, P.L.L.C.

[57] ABSTRACT

Neurokinin-antagonistic compounds corresponding to formula I:

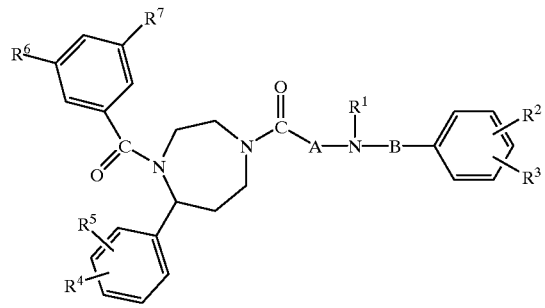

in which
 $R^1$ is hydrogen or lower alkyl,
 $R^2$ is hydrogen, lower alkyl, lower alkoxy, halogen or trifluoromethyl, and
 $R^3$ is hydrogen, lower alkyl, lower alkoxy, halogen or trifluoromethyl, or
 $R^2$ and $R^3$ together are alkylenedioxy with 1 to 2 carbon atoms, bonded to adjacent carbon atoms of the phenyl ring,
 $R^4$ is hydrogen, lower alkyl, lower alkoxy, halogen or trifluoromethyl, and
 $R^5$ is hydrogen, lower alkyl, lower alkoxy, halogen or trifluoromethyl, or
 $R^4$ and $R^5$ together are alkylenedioxy with 1 to 2 carbon atoms, bonded to adjacent carbon atoms of the phenyl ring,
 $R^6$ is lower alkyl, halogen or trifluoromethyl,
 $R^7$ is lower alkyl, halogen or trifluoromethyl,
 A is a $-(CH_2)_n-$ group in which n represents an integer from 1 to 3, or an $-NH-(CH_2)_m-$ group in which m represents an integer from 2 to 3, and
 B is an alkylene chain with 1 to 3 carbon atoms optionally substituted by lower alkyl,
and physiologically acceptable salts thereof and processes for the preparation of these compounds.

6 Claims, No Drawings

7-PHENYL-1, 4-DIAZEPANE COMPOUNDS, PROCESS FOR THEIR PREPARATION, AND PHARMACEUTICAL COMPOSITIONS CONTAINING THEM

BACKGROUND OF THE INVENTION

The present invention relates to novel 7-phenyl-1-benzoyl-1,4-diazepane derivatives which are substituted in the 4 position by a carbonyl group bearing an N-phenylalkyl-aminoalkyl radical or an N-phenylalkylaminoalkylamino radical, and their salts, and also to pharmaceutical preparations and intermediate compounds containing these compounds and to methods for preparing these compounds.

1,4-disubstituted piperazine derivatives having activities antagonistic to tachykinin and neurokinin receptors are known from U.S. Pat. No. 5,670,505 (=EP 655,442).

Neurokinins are neuropeptides which, like their associated receptors, are widespread in the human body and are found in the gastrointestinal tract, in the cardiovascular region and in the CNS region. These are neurotransmitters which have a wide-ranging activity spectrum and which, inter alia, play a part in occurrences of pain, inflammatory processes, vasodilation and contractions of the non-striated muscles, in particular in the gastrointestinal region. Neurokinin-receptor antagonists are pharmacologically active substances which have the ability to bind to neurokinin receptors and thus can inhibit neurokinin-induced processes.

SUMMARY OF THE INVENTION

It is an object of the present invention to provide novel compounds antagonistic to neurokinin receptors.

A further object of the invention is to provide compounds having an activity profile beneficial for the treatment of functional and inflammatory disorders in the Gastrointestinal tract.

It is also an object to provide new compounds for treating functional and inflammatory disorders in the gastrointestinal tract which exhibit good physiological tolerability.

It has now been discovered that the 7-phenyl-1-benzoyl-1,4-diazepane derivatives according to the invention which are substituted in the 4 position by a carbonyl group bearing an N-phenylalkyl-aminoalkyl radical or an N-phenylalkyl-aminoalkylamino radical, have activities antagonistic to neurokinin receptors and are is suitable for the treatment and prophylaxis of pathological conditions caused by substances which bind to neurokinin or tachykinin receptors and are distinguished by a pharmacological activity profile with a marked active component with respect to visceral hypersensitivity to pain and functional disorders of the gastrointestinal tract, in particular in the region of the lower intestinal tracts.

The invention therefore relates to compounds of the central formula I

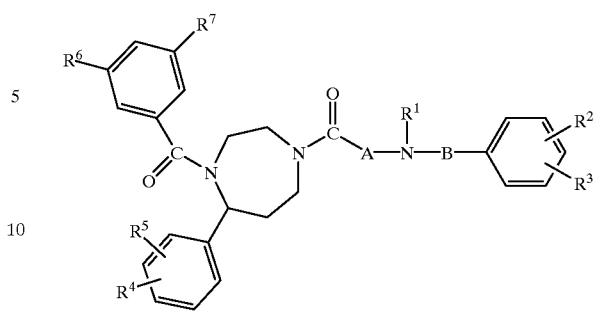

wherein $R^1$ is hydrogen or lower alkyl, $R^2$ is hydrogen, lower alkyl, lower alkoxy, halogen or trifluoromethyl, and $R^3$ is hydrogen, lower alkyl, lower alkoxy, halogen or trifluoromethyl, or $R^2$ and $R^3$ together are alkylenedioxy with 1 to 2 carbon atoms, bonded to adjacent carbon atoms of the phenyl ring, $R^4$ is hydrogen, lower alkyl, lower alkoxy, halogen or trifluoromethyl, and $R^5$ is hydrogen, lower alkyl, lower alkoxy, halogen or trifluoromethyl, or $R^4$ and $R^5$ together are alkylenedioxy with 1 to 2 carbon atoms, bonded to adjacent carbon atoms of the phenyl ring, $R^6$ is lower alkyl, halogen or trifluoromethyl, $R^7$ is lower alkyl, halogen or trifluoromethyl, A is a —$(CH_2)_n$— group in which n stands for an integer from 1 to 3, or an —NH—$(CH_2)_m$— group in which m stands for an integer from 2 to 3, and B is an alkylene chain with 1 to 3 carbon atoms, optionally substituted by lower alkyl, and physiologically compatible acid addition salts thereof.

If in the compounds of Formula I the substituents represent or contain lower alkyl, this may be branched or unbranched, and preferably contain 1 to 4 carbon atoms, and is preferably methyl.

The substituents $R^2$ and $R^3$ may each, independently of each other, preferably represent hydrogen or lower alkoxy, particularly preferably methoxy. If the substituents $R^2$ and/or $R^3$ represent lower alkoxy, the phenyl ring bearing $R^2$ and $R^3$ may preferably be substituted once by lower alkoxy and this may be located in particular in the 2 position of the phenyl ring. If $R^2$ and/or $R^3$ represent halogen, this is preferably chlorine or fluorine, particularly preferably fluorine.

If the substituents $R^4$ and/or $R^5$ represent halogen, fluorine is preferred. Preferably $R^4$ and $R^5$ are hydrogen.

The substituents $R^6$ and R7, independently of each other, each preferably represent trifluoromethyl. If $R^6$ and/or $R^7$ is lower alkyl, this is preferably methyl. If $R^6$ and/or $R^7$ represents halogen, chlorine is preferred.

A may preferably be a —$(CH_2)_n$— group in which n is an integer; particularly preferably n is the number 3.

The alkylene chain B is preferably unsubstituted, and particularly preferably represents a methylene group.

According to the invention, compounds of the general formula I can be obtained by the following process:

a) for the preparation of compounds of the general formula I compounds of the general formula IIa

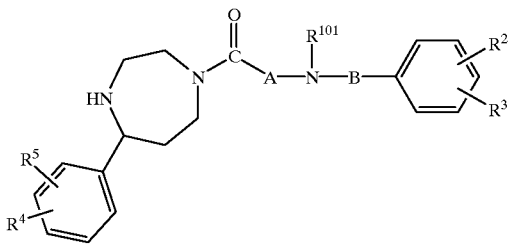

wherein $R^2$, $R^3$, $R^4$, $R^5$, A and B have the above meanings and $R^{101}$ stands for lower alkyl or an amino protective group, are reacted with compounds of the general formula III

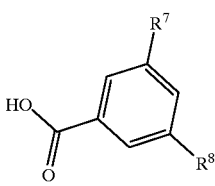

wherein $R^6$ and $R^7$ have the above meanings, and any amino protective group $R^{101}$ is subsequently cleaved off again, or b) for the preparation of compounds of the general formula Ia

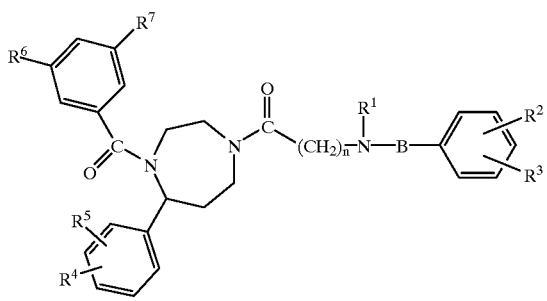

wherein $R^1$, $R^2$, $R^3$, $R^4$, $R^5$, $R^6$, $R^7$, B and n have the above meanings, compounds of the general formula IV

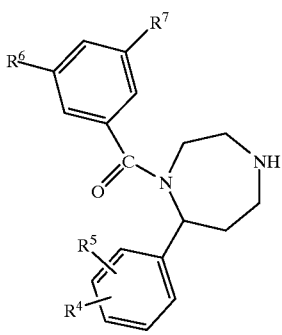

wherein $R^4$, $R^5$, $R^6$ and $R^7$ have the above meanings, are reacted with compounds of the general formula V

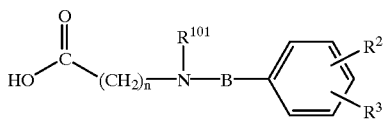

wherein $R^{101}$, $R^2$, $R^3$, B and n have the above meanings, and any amino protective group $R^{101}$ is subsequently cleaved off again, or c) for the preparation of compounds of the general formula Ib

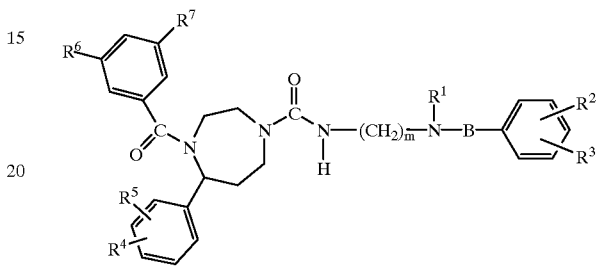

wherein $R^1$, $R^2$, $R^3$, $R^4$, $R^5$, $R^6$, $R^7$, B and m have the above meanings, compounds of Formula IV are reacted with compounds of the general formula VI

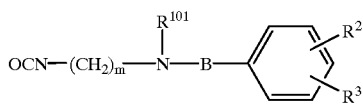

wherein $R^{101}$, $R^2$, $R^3$, B and m have the above meanings, and any amino protective group $R^{101}$ is subsequently cleaved off again, or d) for the preparation of compounds of Formula I, compounds of the general formula VIII

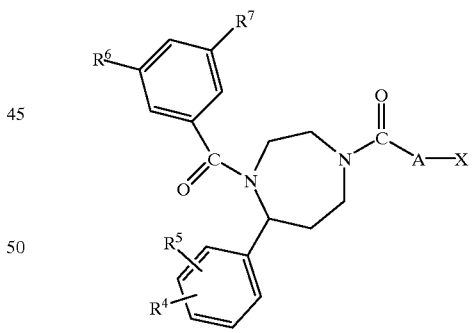

wherein $R^4$, $R^5$, $R^6$, $R^7$ and A have the above meanings and X represents a cleavable leaving group, are reacted with compounds of the general formula IXa

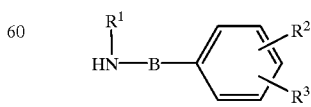

wherein $R^1$, $R^2$, $R^3$ and B have the above meanings, or e) for the preparation of compounds of Formula I, compounds of the general formula X

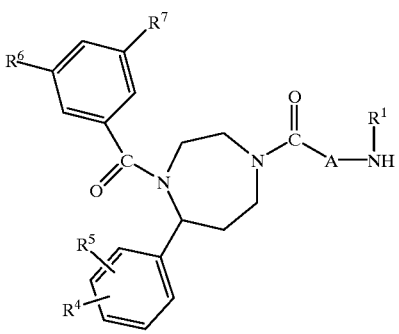

wherein $R^1$, $R^4$, $R^5$, $R^6$, $R^7$ and A have the above meanings, are reacted under conditions of reductive alkylation with compounds of the general formula XIa

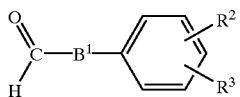

wherein $R^2$ and $R^3$ have the above meanings and $B^1$ represents a bond or an alkylene chain with 1 to 2 carbon atoms, optionally substituted by lower alkyl, or are alkylated with compounds of the general formula XIb

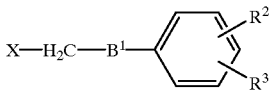

wherein $R^2$, $R^3$, $B^1$ and X have the above meanings, and optionally resulting compounds of Formula I wherein $R^1$ is hydrogen are alkylated to form compounds of Formula I wherein $R^1$ is lower alkyl, or optionally resulting compounds of the general formula I are converted into the acid addition salts thereof or acid addition salts are converted into free compounds of Formula I.

The compounds of Formula I can be prepared in accordance with process variant a) by reacting compounds of Formula IIa with compounds of Formula III by aminoacylation in known manner using conventional methods for the formation of amide groupings and optionally subsequently cleaving off any amino protective group $R^{101}$. The acids of Formula III or their reactive derivatives can be used as acylation agents. In particular, mixed acid anhydrides and acid halides are suitable as reactive derivatives. For example, acid chlorides or acid bromides of the acids of Formula III or mixed esters of the acids of Formula III with chloroformic acid or with organic sulfonic acids, for example lower alkanesulfonic acids such as methanesulfonic acid or aromatic sulfonic acids such as benzenesulfonic acid or benzenesulfonic acids substituted by lower alkyl or halogen, e.g. toluene-sulfonic acids or bromobenzenesulfonic acids, can be used. The acylation can be effected in an organic solvent which is inert under the reaction conditions, preferably at temperatures between –20° C. and room temperature. Suitable solvents include in particular aromatic hydrocarbons such as benzene or toluene, aliphatic ethers such as diethyl ether, tetrahydrofuran (THF) or dioxane, partially halogenated lower hydrocarbons such as dichloromethane or mixtures of these solvents.

The acylation can advantageously be carried out in the presence of an acid-binding reagent, in particular if an acid halide of the acids of Formula III is used as an acylation agent. Suitable acid-binding reagents include non-nucleophilic bases which are soluble in the reaction mixture, such as organic tertiary nitrogen bases, for example nitrogen-containing N-alkylated heterocycles such as N-lower alkyl morpholine or N-lower alkyl piperidine or tertiary lower alkylamines and pyridines, such as triethylamine, tripropylamine, diisopropylethylamine, pyridine, 4-dimethylaminopyridine, 4-diethylaminopyridine or 4-pyrrolidinopyridine. Organic bases used in excess can also be used as solvents at the same time.

If the acids of Formula III themselves are used as acylation agents, the reaction of the amines of Formula IIa with the acids of Formula III can advantageously also be carried out in the presence of a coupling reagent known from peptide chemistry to be suitable for amide formation. Examples of coupling reagents which promote amide formation with the free acids by reacting with the acid in situ to form a reactive acid derivative, include in particular: alkyl carbodiimides, e.g cycloalkyl carbodiimides such as dicyclohexyl carbodiimide or 1-ethyl-3-[(dimethylamino)-propyl]-carbodiimide, diisopropyl carbodiimide, carbonyl diimidazole and N-lower alkyl-2-halopyridinium salts, in particular halides or tosylates. The reaction in the presence of a coupling reagent can advantageously be performed at temperatures between –30° C. and +50° C. in solvents such as halogenated hydrocarbons and/or aromatic solvents such as optionally substituted benzenes, and optionally in the presence of an acid-binding organic compound, for example a non-nucleophilic nitrogen base as described above.

The preparation of compounds of Formula Ia in accordance with process variant b) can be effected by reacting compounds of Formula IV with carboxylic acids of Formula V in known manner under the conditions described above for the reaction of compounds of Formula IIa with compounds of Formula III in accordance with process variant a).

Compounds of Formula Ib can be prepared in accordance with process variant c) by reacting compounds of Formula IV with isocyanates of Formula VI in known manner. The compounds of Formula VI can be obtained, for example, from the amines of the general formula VII

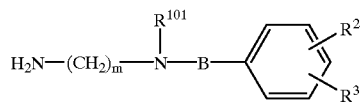

wherein $R^{101}$, $R^2$, $R^3$, B and m have the above meanings by reaction with suitable reactive carbonyl compounds in known manner. Suitable reactive carbonyl compounds include, for example, phosgene or substances which react like phosgene, such as bis-(trichloromethyl)-carbonate (triphosgene), trichloromethyl chloroformate (diphosgene) or carbonyl diimidazole. Advantageously, the compounds of Formula Ib are prepared by first producing isocyanates of Formula VI from amines of Formula VII and then reacting them directly in situ with compounds of Formula IV. The reaction sequence can be carried out as a one-pot reaction in a polar aprotic solvent such as a partially halogenated lower hydrocarbon, for example dichloromethane, at temperatures between –20° C. and room temperature, preferably between 0° C. and room temperature. Advantageously, an acid-binding reagent can be added to the reaction mixture. Suitable acid-binding reagents include the reagents described above for the reaction of compounds of Formula IIa with compounds of Formula III.

Isocyanates of Formula VI can also be obtained from carboxylic acids of Formula V or their reactive derivatives under the conditions of a Curtius degradation. Thus, for example, reactive derivatives of carboxylic acids of Formula V, such as esters, anhydrides or acid halides thereof which can be obtained according to generally conventional processes, can be converted into the corresponding isocyanates in known manner by reaction with alkali metal azides such as sodium azide and subsequent heating. Likewise, the acids of Formula V can be reacted by reaction with diphenylphosphoryl azide or a similarly acting reagent in order to obtain isocyanates of Formula VI. Advantageously, this reaction sequence also can be carried out as a one-pot reaction in a polar aprotic solvent which is inert under the reaction conditions, such as dimethyl formamide (DMF), dimethyl sulfoxide (DMSO) or an aliphatic ether such as THF or dioxane. Advantageously, an acid-binding reagent can first be added to the reaction mixture at temperatures between 10 and 40° C., and then to complete the conversion the mixture may be heated to temperatures between 80 and 120° C., preferably to 100° C. The acid-binding reagents described above for the reaction of compounds of Formula IIa with compounds of Formula III can be used as acid-binding reagents.

Compounds of Formula I can also be prepared in accordance with process variant d) by reacting compounds of Formula VIII with compounds of Formula IXa in known manner under generally conventional conditions for nucleophilic substitution reactions. Suitable cleavable leaving groups X in compounds of Formula VIII include halogens, in particular chlorine, bromine and iodine, or an organic sulfonic acid radical, for example the radical of a lower alkanesulfonic acid such as methanesulfonic acid, or of aromatic sulfonic acids such as benzenesulfonic acid, or of benzenesulfonic acids substituted by lower alkyl or halogen, such as toluenesulfonic acids. The reaction can be performed in a polar aprotic solvent such as DMF, DMSO or acetonitrile at temperatures between −20° C. and 100° C., preferably between 60° C. and 90° C., and using an acid-binding reagent. Suitable acid-binding reagents include, for example, the acid-binding reagents described above for the reaction of compounds of Formula IIa with compounds of Formula III.

Another possible method of preparing the compounds of Formula I is the alkylation of compounds of Formula X with compounds of Formula XIa or XIb in accordance with process variant e). If compounds of Formula XIa are used, the reaction can be performed using conventional methods for the reductive alkylation of amines. In this case, the reducing agents and reduction conditions must be selected such that amide carbonyl groups present in the molecule are not attacked. For example, the reaction can be carried out under the conditions of catalytic hydrogenation. The catalytic hydrogenation can be effected in an organic solvent which is inert under the reaction conditions, such as a lower aliphatic ether, for example THF or diethyl ether, a lower alkanol, for example methanol or ethanol, or in mixtures of these solvents and in the presence of a hydrogenation catalyst. Suitable hydrogenation catalysts include preferably metal catalysts such as Raney nickel. Advantageously, the reaction is carried out at room temperature. A hydrogen pressure suitable for hydrogenation may be between normal pressure and a hydrogen pressure of 5 bar, preferably between 2 and 4 bar.

If compounds of Formula XIb are used, the reaction can be performed under generally conventional conditions for nucleophilic substitution reactions. Thus, for example, the conditions given above for reactions of compounds of Formula VIII with compounds of Formula IXa in accordance with process variant d) may be selected.

If in the preparation of compounds of Formula I or of their intermediate products, free amino groups are protected by amino protective groups, amino protective groups which are known per se, for example from peptide chemistry, and which can be introduced and cleaved off again using known methods, can be considered within the scope of the invention. Suitable protective groups are known, for example, from J. A. W. McOmie "Protective Groups in Organic Chemistry", Plenum Press 1973, or T. W. Green and P. G. M. Wuts "Protective Groups in Organic Synthesis", Wiley and Sons 1991.

Preferably, groups which are largely stable in acid and in alkaline media and which can be cleaved off again under hydrogenolytic conditions can be used as amino protective groups $R^{101}$. The cleaving of the protective group can be effected under conditions under which desired phenyl lower alkylamino groups optionally substituted in the phenyl ring, which may optionally be present in the molecule, are retained. For example, phenyl lower alkyloxycarbonyl groups, preferably the benzyloxycarbonyl group, are suitable as amino protective groups $R^{101}$. These can be cleaved in known manner, e.g. by catalytic hydrogenation, in order to obtain compounds of Formula I wherein $R^1$ is hydrogen. The reaction can be effected in an organic solvent which is inert under the reaction conditions, such as a lower aliphatic ether, for example THF or diethyl ether, lower alkanols, for example methanol or ethanol, or organic acids, for example lower aliphatic carboxylic acids such as acetic acid, or in mixtures of these solvents and in the presence of a hydrogenation catalyst. Suitable hydrogenation catalysts include precious metal catalysts such as palladium on activated carbon. Advantageously, the reaction is carried out at room temperature. A hydrogen pressure suitable for hydrogenation is between 3 and 7 bar, preferably between 4 and 6 bar.

The compounds of Formula I, in which $R^1$ is hydrogen, may if desired be converted according to known methods for aminoalkylation into compounds of Formula I in which $R^1$ is lower alkyl. For this, the compounds of Formula I may, for example, be reductively alkylated by reaction with lower aliphatic aldehydes such as formaldehyde under the conditions given above for the reaction of compounds of Formula X with compounds of Formula XIa. Another possible method of alkylation is the reaction of compounds of Formula I in which $R^1$ is hydrogen with lower aliphatic alkyl halides such as alkyl bromides or alkyl iodides, preferably methyl iodide, alkyl sulfates or alkylsulfonic acid esters, using the method given above for the reaction of compounds of Formula VIII with compounds of Formula IXa. Suitable acid-binding reagents are the acid-binding reagents described above for the reaction of compounds of Formula IIa with compounds of Formula III.

Physiologically acceptable salts of compounds of Formula I include their salts with inorganic acids, for example sulfuric acid, phosphoric acids or hydrohalic acids, preferably hydrochloric acid, or with organic acids, for example lower aliphatic monocarboxylic, dicarboxylic or tricarboxylic acids such as maleic acid, fumaric acid, lactic acid, tartaric acid, citric acid, or with sulfonic acids, for example lower alkanesulfonic acids such as methanesulfonic acid or benzenesulfonic acids optionally substituted in the benzene ring by halogen or lower alkyl, such as p-toluenesulfonic acid.

The compounds of Formula I can be isolated from the reaction mixture and purified in known manner. Acid addition salts can be converted into the free bases in conventional manner, and these may if desired be converted in known manner into pharmacologically compatible acid addition salts.

The compounds of Formula I contain an asymmetric or chiral carbon atom, namely the carbon atom bearing the phenyl ring substituted by $R^4$ and $R^5$ in the 7 position of the 1,4-diazepane parent structure. If B represents an alkylene chain substituted one or more times by lower alkyl, at least one additional asymmetric center may be added. The compounds of Formula I can thus be present in several stereoisomeric forms. The present invention includes both the mixtures of optical isomers and the isomerically pure compounds of Formula I.

If mixtures of optical isomers of the starting compounds of Formula IIa, IV, VIII or X are used in the synthesis of the compounds of Formula I, the compounds of Formula I are also obtained in the form of mixtures of optical isomers. Starting from stereochemically uniform starting compounds, stereochemically uniform compounds of Formula I can also be obtained. The stereochemically uniform compounds of Formula I can be obtained from the mixtures of optical isomers in a known manner, for example diastereomers of Formula I can be separated by chromatographic separation methods or by fractional crystallization, and enantiomers of Formula I can be obtained, for example, by chromatographic separation on chiral separating materials.

The compounds of Formula II

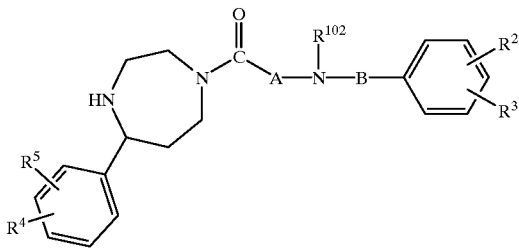

wherein $R^2$, $R^3$, $R^4$, $R^5$, A and B have the above meanings and $R^{102}$ is hydrogen, lower alkyl or an amino protective group, are novel compounds, and represent valuable intermediate products for the preparation of pharmaceutically effective compounds, e.g. the compounds of Formula I. The compounds of Formula II can be obtained in known manner.

Thus compounds of Formula IIa wherein A represents a —(CH$_2$)$_n$— group in which n has the above meaning can be obtained by reacting carboxylic acids of Formula V or their reactive derivatives with compounds of the general formula XIIa

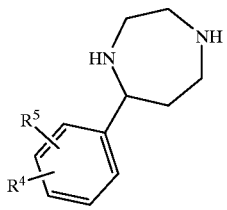

wherein $R^4$ and $R^5$ have the above meanings, for example in accordance with the processes given above for the acylation of amines of Formula IIa with carbocyclic acids of Formula III.

Compounds of Formula IIa wherein A represents an —NH—(CH$_2$)$_m$— group in which m has the above meaning can be prepared by reacting compounds of Formula VI with compounds of the general formula XIIb

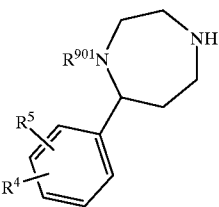

wherein $R^4$ and $R^5$ have the above meanings and $R^{901}$ stands for an amino protective group, in accordance with the processes given above for the reaction of compounds of Formula IV with compounds of Formula VI, and subsequently cleaving off the protective group $R^{901}$ again. Groups which can be cleaved selectively preferably in acidic medium, for example due to the addition of p-toluenesulfonic acid, trifluoroacetic acid or gaseous hydrochloric acid or hydrochloric acid dissolved in water, and which are largely stable against reductive, in particular hydrogenolytic and alkaline, conditions are suitable as protective groups $R^{901}$. These include, for example, the triphenylmethyl(=trityl) group and branched lower alkyloxycarbonyl groups such as the tert.butyloxycarbonyl group. Preferably the tert.butyloxycarbonyl group (abbreviated to BOC group below) can be used as amino protective group $R^{901}$.

The intermediate products of Formula IIa can also be prepared by reacting compounds of the general formula XIII

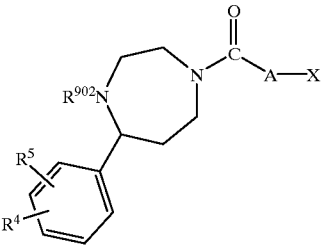

wherein $R^4$, $R^5$, A and X have the above meanings and $R^{902}$ stands for an amino protective group, with compounds of the general formula IXb

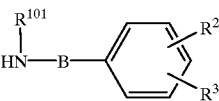

wherein $R^{101}$, $R^2$, $R^3$ and B have the above meanings, according to the process given above for the reaction of compounds of Formula VIII with the amines of Formula IXa and subsequent cleaving of the amino protective group $R^{902}$. Amino protective groups which can preferably be cleaved off again by catalytic hydrogenation are suitable as protective group $R^{902}$. Suitable hydrogenation catalysts for this purpose include, for example, precious metal catalysts such as palladium on activated carbon or palladium hydroxide on activated carbon. Preferably $R^{902}$ may be the benzyl group. If desired, the amino protective group can be cleaved off in known manner from compounds of Formula IIa wherein $R^{101}$ represents an amino protective group in order to release the —NH— group, which means that compounds of Formula II can be obtained in which $R^1$ is hydrogen. The compounds of Formula IXb wherein $R^{101}$ stands for an amino protective group represent protected derivatives of the amines of Formula IXa, and can be prepared from amines of Formula IXa wherein $R^1$ stands for hydrogen by known introduction of a protective group $R^{101}$. The amines of Formula IXa are known, or can be prepared from known compounds in known manner.

The compounds of Formula IV are novel, and represent valuable intermediate products for the preparation of pharmaceutically active compounds, for example the compounds of Formula I. The compounds of Formula IV can be prepared in accordance with known methods.

Thus, the diazepane derivatives of Formula IV can, for example, be obtained by known reduction of the diazepanone derivatives of the general Formula XIV

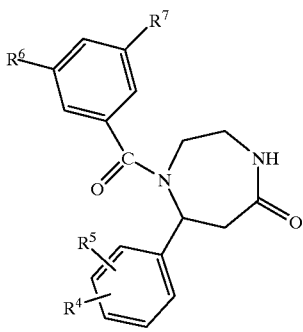

wherein $R^4$, $R^5$, $R^6$ and $R^7$ have the above meanings. The reduction of the carbonyl group contained in the diazepane ring structure car be performed selectively by first adding an alkylation reagent such as a tri-lower alkyloxonium salt, for example triethyloxonium tetrafluoroborate, to the compounds of Formula XIV, and then reacting the intermediate product produced upon the reaction with the reducing agent, with the introduced alkyl group being cleaved off again. Alkali metal borohydrides such as sodium borohydride can be used as reducing agents. The reaction with the alkylation agent can be carried out in an aprotic solvent such as a partially halogenated lower hydrocarbon, for example dichloromethane, a lower alkyl cyanide, for example acetonitrile, or a di-lower alkyl ether such as dioxane, THF or diethyl ether. The reaction temperature can advantageously lie between –20° C. and approximately 60° C., preferably room temperature. It is advantageous to isolate the intermediate product produced by reaction with the alkylation reagent, for example by at least partially evaporating the original solvent, and then re-dissolving it in a polar protic solvent such as a lower alkanol, for example methanol or ethanol. A temperature suitable for performing the reduction step is between –20° C. and 60° C., and it is preferable to operate at room temperature.

The compounds of Formula VIII are novel, and represent valuable intermediate products for the preparation of pharmaceutically active compounds, e.g. the compounds of Formula I. The compounds of Formula VIII can be prepared in accordance with known methods.

Thus, for example, compounds of Formula VIII wherein A represents a —$(CH_2)_n$— group in which n has the above meaning can be prepared by reacting compounds of Formula IV with known ω-halocarboxylic acids of the general formula XV

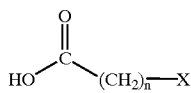

wherein X and n have the above meanings, or their reactive derivatives, in accordance with the processes given above for the reaction of carboxylic acids of Formula III with the amines of Formula IIa.

Compounds of Formula VIII wherein A represents an —NH—$(CH_2)_m$— group in which m has the above meaning can be prepared by reacting compounds of Formula IV with isocyanates of the general formula XVI

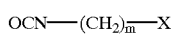

wherein X and m have the above meanings, in accordance with the processes given above for the reaction of isocyanates of Formula VI with amines of Formula IV. The isocyanates of Formula XVI are known, or can be prepared according to known methods from the corresponding amines of the general formula XVII

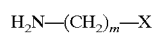

wherein X and m have the above meanings. For example, the amines of Formula XVII can be converted into the isocyanates of Formula XVI in the manner described above for the reaction of the amines of Formula VII to isocyanates of Formula VI.

The compounds of Formula X are novel, and represent valuable intermediate products for the preparation of pharmaceutically active compounds, e.g. the compounds of Formula I. The compounds of Formula X can be prepared in accordance with known methods.

Thus, for example, compounds of Formula X wherein A represents a —$(CH_2)_n$— group in which n has the above meaning can be prepared by reacting the amines of Formula IV with carboxylic acids of the general formula XVIIIa

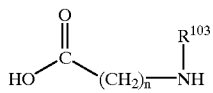

wherein n has the above meaning and $R^{103}$ has the meaning given for $R^{901}$, in accordance with the processes given above for reactions of the amines of Formula IIa with carboxylic acids of Formula III, and then cleaving off the protective group $R^{103}$ in known manner. The acids of Formula XVIIIa represent amino-protected ω-aminocarboxylic acids which are known in unprotected form and which can be prepared in accordance with known methods.

Compounds of Formula X wherein A represents a —$(CH_2)_n$— group in which n has the above meaning can also be prepared by reacting compounds of Formula III with compounds of the general formula XIX

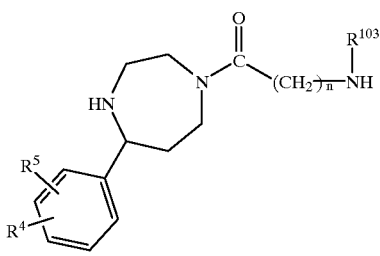

wherein $R^{103}$, $R^2$, $R^3$ and n have the above meanings, and then cleaving off the protective group $R^{103}$ again in known manner. The reaction can be performed according to known methods for amide formation. For example, the reaction can be performed in accordance with the process given above for the reaction of compounds of Formula IIa with compounds of Formula III.

Compounds of Formula X wherein A represents an —NH—$(CH_2)_m$— group in which m has the above meaning can be prepared by reacting the amines of Formula IV with isocyanates of the general formula XX

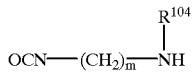

wherein m has the above meaning, and $R^{104}$ may have the meaning given for $R^{901}$ or $R^{902}$, in accordance with the process described above for the reaction of the amines of Formula IV with the isocyanates of Formula VI, and subsequently cleaving of f the protective group $R^{104}$ again in known manner. The isocyanates of Formula XX can be prepared according to the method given above for the preparation of the isocyanates of Formula VI from the amines of Formula VII, from amines of the formula XXI

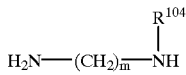

wherein $R^{104}$ and m have the above meanings. The compounds of Formula XXI represent singly amino-protected 1-ω-diaminoalkanes, which are generally known in unprotected form and which can be prepared from the unprotected precursor compounds using known methods. For example, the singly amino-protected amines of Formula XXI can be obtained from the corresponding unprotected diaminoalkanes by reacting one mole equivalent of the diamine with one mole equivalent of the reagent required for introducing the protective group.

The carboxylic acids of Formula V used for preparing compounds of Formula IIa can, for example, be prepared in a known manner for the reductive alkylation of amines from the ω-aminocarboxylic acids of the general formula XVIIIb

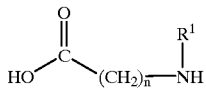

wherein $R^1$ and n have the above meanings, by reaction with the aldehydes of the general formula XIa and, if $R^1$ stands for hydrogen, subsequent introduction of an amino protective group $R^{101}$. For example, the reductive alkylation can be performed in aqueous alkaline solution, for example in 1-normal aqueous sodium hydroxide solution. The addition of a solubiliser such as a water-soluble organic solvent, for example a lower alkanol such as methanol, may be advantageous here. Suitable temperatures for the reaction lie between −10° C. and 60° C., preferably between 5° C. and room temperature. Complex hydrides such as alkali metal borohydrides, preferably sodium borohydride or sodium cyanoborohydride, are suitable as reducing agents. Likewise, the reductive alkylation can be carried out under hydrogenolytic conditions. The hydrogenolysis can be performed under the conditions given above for the hydrogenolytic cleaving of amino protective groups $R^{101}$ from compounds of Formula I. Compounds of Formula XVIIIb are known, or can be prepared from known compounds by known methods.

The amines of Formula VII suitable for preparing the isocyanates of Formula VI can be obtained from the 1-N-amino-protected compounds of the general formula XXII

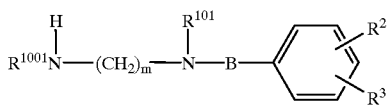

wherein $R^{101}$, $R^2$, $R^3$, B and m have the above meanings and $R^{1001}$ has the meaning given for $R^{901}$, by selectively cleaving off the amino protective group $R^{1001}$ from compounds of Formula XXII in known manner under conditions in which the protective group $R^{101}$ is not attacked. For example, the protective group $R^{1001}$ can be cleaved off under acidic conditions.

Compounds of Formula XXII can be obtained by reducing amides of the general Formula XXIII

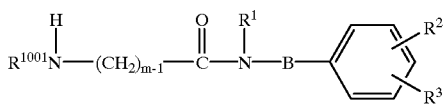

wherein $R^1$, $R^2$, $R^3$, $R^{1001}$, B and m have the above meanings, and subsequently introducing an amino protective group $R^{101}$ into compounds in which $R^1$ stands for hydrogen. The reduction can be effected with complex alkali metal hydrides, such as lithium aluminium hydride, as reducing agent. Suitable solvents include organic solvents which are inert under the reaction conditions, such as lower aliphatic ethers, for example dioxane, THF or diethyl ether. A suitable temperature range is between −20° C. and the boiling temperature of the reaction mixture. The reduction is preferably carried out at room temperature. The amides of Formula XXIII can be prepared by reacting amino-protected ω-aminocarboxylic acids of the general Formula XXIV

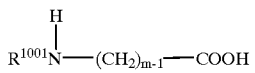

wherein $R^{1001}$ and m have the above meanings, with the amines of Formula IXa using conventional methods for amide formation. For example, the amide formation can be carried out according to the process described above for the reaction of compounds of Formula IIa with compounds of Formula III. The acids of Formula XXIV represent amino-protected ω-aminocarboxylic acids, which are generally known in unprotected form and which can be prepared in accordance with known methods from the unprotected precursor compounds.

Amines of Formula VII wherein m represent the number 3 can in particular also be prepared by reducing cyanides of the general formula XXV

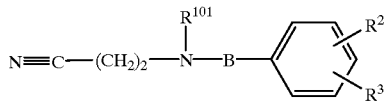

wherein $R^{101}$, $R^2$, $R^3$ and B have the above meanings, in known manner. The reduction can be effected by catalytic hydrogenation, with metal hydrogenation catalysts such as Raney nickel being suitable as catalysts. Suitable solvents include polar organic solvents which are inert under the reaction conditions, such as lower alkanols, for example methanol or ethanol. Usually the reaction is performed at room temperature and at a pressure of 1 to 3 bar, preferably about 2 bar. In order to avoid secondary reactions, a sufficient quantity of a concentrated aqueous ammonia solution can be added to the reaction solution before the addition of the catalyst.

The cyanides of Formula XXV can be prepared by reacting acrylonitrile of Formula XXVI

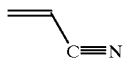

with amines of Formula IXb. The reaction can be carried out under known conditions suitable for performing Michael additions. Polar aprotic solvents which are inert under the reaction conditions, such as DMF, DMSO or dichloromethane, can be used as solvents. Usually, the reaction is performed at temperatures between −20° C. and 60° C., preferably at room temperature. In order to accelerate the reaction, it is advantageous to add a suitable catalyst to the reaction mixture. Suitable catalysts include strong bases such as quaternary alkyl- or phenyl-lower alkylammonium hydroxides, for example benzyltrimethylammonium hydroxide.

The diazepanes of Formula XIIa can be obtained in known manner, for example by reduction of the diazepanones of the general Formula XXVIIa

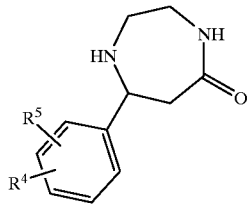

wherein $R^4$ and $R^5$ have the above meanings. The reduction can be performed in accordance with the process given above for the reduction of amides of Formula XXIII.

The compounds of Formula XXVIIa are partially known from C. H. Hofmann, S. R. Safir, Journal of Organic Chemistry 27 (1962), pages 3565 to 3568, and can be obtained by the processes described therein or by processes analogous thereto. For example, the diazepanones of Formula XXVIIa can be prepared by known catalytic hydrogenation of the diazepinones of the general Formula XXVIII

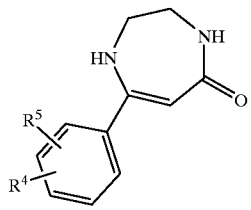

wherein $R^4$ and $R^5$ have the above meanings.

The resulting diazepanones of Formula XXVIIa contain an asymmetric center on the carbon atom bearing the phenyl group. Usually the diazepanones of Formula XXVIIa are obtained upon preparation as racemates. Racemic mixtures of compounds of Formula XXVIIa can be separated into their optical isomers in known manner, for example by reaction with suitable optically active acids, such as 10-camphorsulfonic acid, and subsequent separation into their optically active antipodes by fractional crystallization of the resulting diastereomeric salts.

The compounds of Formula XXVIII can be prepared in known manner, such as, for example, by condensation of ethylenediamine with the ethyl benzoylacetates of the general formula XXIX

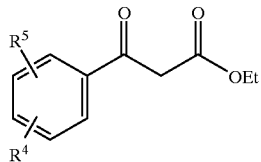

wherein $R^4$ and $R^5$ have the above meanings.

The compounds of Formula XIIb can be obtained from the diazepanone compounds of the general formula XXVIIb

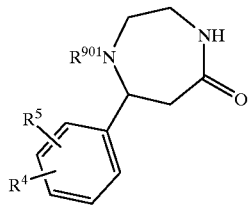

wherein $R^4$, $R^5$ and $R^{901}$ have the above meanings, in known manner by reduction. The reduction can, for example, be performed according to the method described above for the reduction of amides of Formula XXIII. The compounds of Formula XXVIIb can be obtained by introducing suitable protective groups into compounds of Formula XXVIIa.

Compounds of Formula XIII used in the synthesis of intermediate products of Formula IIa and in which A stands for a —$(CH_2)_n$— group in which n has the above meaning can be prepared by reacting compounds of the general formula XIIc

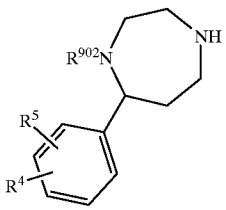

wherein $R^4$, $R^5$ and $R^{902}$ have the above meanings, with carboxylic acids of Formula XV under conventional conditions for aminoacylation. In particular, the amide formation can be carried out in accordance with the process given above for the reaction of compounds of Formula IIa with compounds of Formula III.

Compounds of Formula XIII wherein A stands for an —NH—$(CH_2)_m$— group in which m has the above meaning can be prepared by reacting the amines of Formula XIIc with isocyanates of Formula XVI. The reaction can be carried out in the manner described above for the reaction of amines of Formula IV with isocyanates of Formula VI.

Singly amino-protected diazepane derivatives of Formula XIIc can be obtained in known manner by reduction from the singly amino-protected diazepanones of the general formula XXVIIc

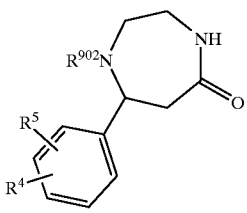

wherein $R^4$, $R^5$ and $R^{902}$ have the above meanings. The reduction can be effected analogously to the process described above for the reduction of amides of Formula XXIII. The amino-protected diazepanones of Formula XXVIIc can be obtained by known introduction of suitable amino protective groups from the diazepanones of Formula XXVIIa.

The singly amino-protected diazepanes of Formula XIIc can also be obtained by selective removal of only one amino protective group from bis-amino-protected diazepanes of the general formula XIId

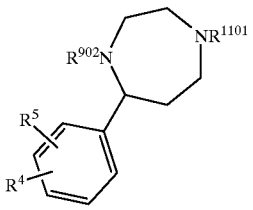

wherein $R^4$, $R^5$ and $R^{902}$ have the above meanings and $R^{1101}$ has the meaning given for $R^{902}$. If, for example, $R^{902}$ and $R^{1101}$ both stand for the benzyl group, selectively only the benzyl group $R^{1101}$ can be cleaved off by reacting compounds of Formula XIId with a chloroformic acid derivative, such as 1-chloroethyl chloroformate, in a polar aprotic solvent which is inert under the reaction conditions, such as a lower alkylcyanide, for example acetonitrile, a partially halogenated lower alkane, for example dichloromethane, a di-lower alkyl ether such as THF, dioxane or diethyl ether or other aprotic solvents such as DMF or DMSO, and then cleaving the resulting intermediate product by adding a suitable reagent to form the desired product. If 1-chloroethyl chloroformate is used, lower alkanols such as methanol are suitable as reagents for cleaving to form the product. Advantageously, at the beginning of the reaction, during the mixing of the reactants, a lower temperature, for example between −20° C. and 10° C., preferably between −5° C. and 5° C., is selected, then the reagent suitable for cleaving to form the product, for example methanol, is added, and then in order to complete the reaction the temperature is increased to 30° C. to 70° C., preferably to 40° C. to 50° C. Advantageously, the volume of the reaction mixture can be reduced in known manner, for example by about one third, before the addition of the reagent.

Bis-amino-protected diazepanes of Formula XIId can for example be prepared by condensing the diamines of the general formula XXX

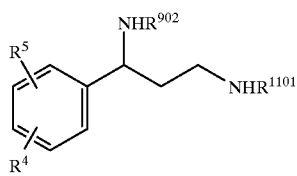

wherein $R^4$, $R^5$, $R^{902}$ and $R^{1101}$ have the above meanings, with glyoxal of Formula XXXI,

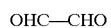

OHC—CHO under conditions generally conventional for the reductive alkylation of amines. Suitable reducing agents include, for example, complex alkali metal borohydrides such as sodium cyanoborohydride. Suitable solvents include polar organic solvents such as lower alkanols, for example methanol or ethanol. Usually the reaction can be performed at temperatures between −20° C. and approximately 60° C., preferably at room temperature.

Diamines of Formula XXX wherein $R^{902}$ represents the benzyl group can be prepared using generally conventional processes, for example by reduction with complex alkali metal hydrides, from the compounds of the general formula XXXII

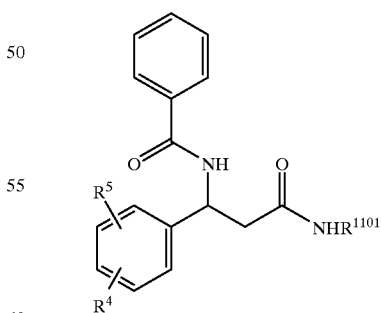

wherein $R^4$, $R^5$ and $R^{1101}$ have the above meanings. The reduction may for example take place according to the process described above for the reduction of amides of Formula XXIII. Bis-amino-protected compounds of Formula XXX wherein the amino protective groups $R^{902}$ and/or $R^{1101}$ have meanings other than benzyl groups can for example be obtained by introducing the desired protective groups into suitable precursor compounds of the compounds of Formula XXX.

The compounds of Formula XXX contain an asymmetric carbon atom and may be present in the form of two different enantiomers. If the starting materialpoint is a pure starting compound, for example a compound of Formula XXXIII, pure isomers of compounds of Formula XXX are also produced.

Compounds of Formula XXXII can be prepared from the amino-acylated 3-amino-3-phenylpropionic acids of the general formula XXXIII

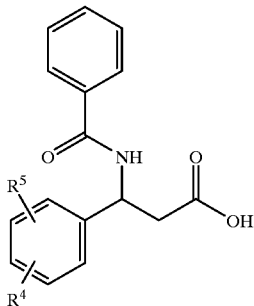

wherein $R^4$ and $R^5$ have the above meanings, by reaction with the amines of the general formula XXXIV

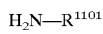

wherein $R^{1101}$ has the above meaning. The reaction can be carried out according to conditions generally conventional for amide formation, for example according to the process given above for the reaction of compounds of Formula IIa with compounds of Formula III.

The compounds of Formula XXXIII can be prepared by known benzoylation of the amino group of 3-amino-3-phenylpropionic acids of the general formula XXXV

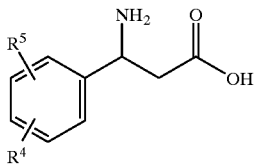

wherein $R^4$ and $R^5$ have the above meanings. If compounds of Formula XXX are desired, wherein $R^{902}$ is an amino protective group other than the benzyl group, these other amino protective groups or their precursors, which can be converted into the corresponding amino protective groups by reduction with complex alkali metal hydrides, may advantageously already be introduced into amines of Formula XXXV.

The compounds of Formula XXXIII contain an asymmetric carbon atom and may occur in the form of two different enantiomers. If racemic mixtures of compounds of Formula XXXV are used in the preparation of compounds of Formula XXXIII, racemic mixtures of compounds of Formula XXXIII are also produced. To prepare pure enantiomers of the compounds of Formula XXX, pure enantiomers of Formula XXXIII can advantageously be used as starting materials. Pure enantiomers of the compounds of Formula XXXIII can be obtained by known separation of their racemic mixtures. The separation can take place by chromatographic separation on chiral separating materials or by reaction with suitable optically active bases, such as α-methylbenzylamine and subsequent separation into the optically active antipodes by fractional crystallization of the resulting diastereomeric salts.

Compounds of Formula XXXV can be prepared by known condensation of aromatic aldehydes of the general formula XXXVI

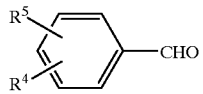

wherein $R^4$ and $R^5$ have the above meanings, with malonic acid of Formula XXXVII

or the lower alkyl esters thereof, and an ammonium salt, for example ammonium acetate. The reaction can be performed in a polar protic organic solvent such as a lower alkanol, for example methanol or ethanol, and at temperatures between room temperature and the boiling point of the reaction mixture, preferably between 70° C. and 90° C.

Compounds of Formula XXXV can also be prepared from α-amino acids of the general formula XXXVIII

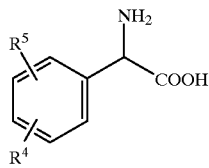

wherein $R^4$ and $R^5$ have the above meanings, in a known manner for chain extension of carboxylic acids by one methylene group. The extension by one methylene unit can be effected, for example, by converting the carboxyl groups of compounds of Formula XXXVIII, for example by reduction with complex metal hydrides such as lithium aluminium hydride, into methylene hydroxy groups, and converting resulting hydroxyl groups in known manner into readily leaving groups such as sulfonic acid esters, for example a trifluoromethylsulfonic acid ester. These leaving groups can then be substituted using alkali metal cyanides such as sodium cyanide by the cyano group, which can be hydrolysed to form the carboxyl group under the conditions conventional for this, in order to obtain aminopropionic acids of Formula XXXV. If the starting point is optically active amino acids of Formula XXXVIII, optically active amino acids of Formula XXXV are also obtained.

The starting compounds of Formula XIV used for the preparation of compounds of Formula IV can be prepared by reacting compounds of Formula III with compounds of Formula XXVIIa according to the method given above for the reaction of compounds of Formula IIa with compounds of Formula III.

Compounds of Formula XIX can be obtained under conditions generally known for aminoacylation, for example according to the method described above for the reaction of compounds of Formula IIa with compounds of Formula III by reacting the singly amino-protected diazepanes of Formula XIIc with the carboxylic acids of Formula XVIIIa and subsequently selectively cleaving off the amino protective group $R^{902}$ in a known manner.

As a result of the reactions of chiral compounds of Formulas XXVIIa, XXXIII, XXXV, XXXVIII or of chiral compounds containing alkylene chains B or $B^1$ substituted one or more times by lower alkyl, as listed above, no changes occur to the asymmetric centers contained therein in each case. The optically pure starting compounds of Formulas XXVIIa, XXXIII, XXXV, XXXVIII and compounds containing alkylene chains B or $B^1$ substituted by lower alkyl therefore also produce optically pure resulting products, in particular optically pure compounds of Formula I.

The compounds of the general formula I and the physiologically acceptable salts thereof have interesting pharmacological properties and are distinguished by a high affinity to neurokinin receptors, predominantly NK-1 receptors. Due to their properties which are antagonistic to neurokinin receptors, the substances are suitable for the treatment of pathological conditions induced by neurokinins. For example, the substances are suitable for the inhibition of processes which are induced by neurokinins which bind to NK-1 receptors in the transmission of pain, emesis, neurogenic inflammations and asthmatic complaints. In this case, the substances display an activity profile beneficial for the treatment of functional and inflammatory disturbances in the gastrointestinal tract and also nausea. The functional disturbances which can be treated with the compounds according to the invention include in particular the disturbances of the lower intestinal tracts known as so-called "irritable bowel syndrome" (=IBS). The essential symptoms of IBS are pains in the lower abdomen, which are substantially caused due to hypersensitivity of the visceral afferent nervous system, and anomalies in bowel movement, in particular abnormally accelerated passage of the stool in the colon. The increased visceral sensitivity to pain with respect to mechanical or chemical stimuli in the intestinal tract results in IBS patients suffering severe visceral pains even upon only slight physiological distension of the colon due to digestion, e.g. even upon slight gas formation and slight flatulence, which are scarcely noticed by healthy individuals. Neurokinins which bind to NK-1 receptors are heavily involved as neurotransmitters in transmission of pain in the gastrointestinal region. The neurokinin-antagonistic active substances according to the invention have a marked beneficial activity profile with respect to visceral pain and disturbances of stool passage in the colon and also nausea. Inflammatory disturbances in the gastrointestinal tract which can be favourably influenced by the compounds according to the invention include the inflammatory disturbances in the small intestine and large intestine regions generally grouped under the term IBD (=inflammatory bowel disease), including ulcerative colitis and Crohn's disease. The activity profile of the substances is distinguished by high selectivity of gastrointestinal and antiemetic effectiveness and good compatibility with a beneficial relationship of gastrointestinal effectiveness to cardiovascular calcium-antagonistic side-effects, and also by good oral effectiveness.

Description of the Pharmacological Test Methods

1. Determination of the binding power of the test substances to NK-1 receptors.

The affinity of the test substances to human NK-1 receptors was measured in vitro, and the inhibition of the binding of the physiological neurokinin substance P to neurokinin-1 receptors was determined.

The receptor binding studies were performed with [$^3$H]-substance P as ligand. For the binding test, different samples of a membrane preparation of CHO cells (=egg cells of the Chinese hamster, Chinese hamster oocytes), which express the human NK-1 receptor, were incubated with a solution of the marked ligand, with the incubation mixtures containing no test substance or additions of different concentrations of test substance. Then, bound and free ligands in each of the samples were separated with the aid of glass-fiber filtration. The fraction remaining in the filter was washed several times with buffer solution, and then the radioactivity of the fraction remaining in the filter was measured using a beta scintillation counter. That concentration which effects half maximum displacement of the bound ligand was determined as $IC_{50}$ of the respective test substance. From this, the corresponding inhibition constant ($K_i$ value) of the test substance was calculated.

The following Table 1 shows $K_i$ values for the affinity of the test substances to human NK-1 receptors, obtained according to the method described above. The example numbers listed for the compounds of Formula I relate to the following preparative examples.

TABLE 1

| Binding affinity to human NK-1 receptors | |
|---|---|
| Example No. | In vitro binding to human NK-1 receptors - $K_i$ value in µmole/l |
| 1 | $K_i = 0.012$ |
| 2 | $K_i = 0.010$ |
| 4 | $K_i = 0.008$ |
| 14 | $K_i = 0.010$ |

2. Investigation of the activity of the compounds on stool passage through the colon of the rat.

The effects of the test substances on the transport of stools through the large intestine were examined in rats after feeding. After feeding, the beginning of elimination and the mean dwell time of barium sulfate in the colon were determined as a measurement of the colon motility leading to elimination of stools.

After oral administration of the test substance, the animals were administered 2 ml of an 80% barium sulfate suspension via an artificial outlet at the caecum. The animals were placed in metabolism cages, and the faeces were collected at one hour intervals over 24 hours. The content of barium sulfate in the faeces was measured using radiography, and the beginning of elimination of barium sulfate and the mean retention time were determined therefrom. The delays in the beginning of elimination and prolongations of the mean residence time of the barium sulfate achieved in this experimental arrangement with various doses of the test substance of Example 1 can be seen from the following Table 2. The time interval up to the beginning of elimination and the mean retention time are given in percentages relative to the values obtained in a control test without test substance (=100%).

TABLE 2

| Influencing of colon passage | | |
|---|---|---|
| Dose of test substance of Example 1 | Time interval until beginning of elimination in % relative to control value = 100% | Mean retention time in % relative to control value = 100% |
| 10 µmole/kg | 100 | 98 |
| 21.5 µmole/kg | 115 | 106 |
| 100 µmole/kg | 138 | 119 |

The test results show that the test substance is capable of depressing the colon activity leading to elimination of faeces.

3. Investigation of the activity of the compounds on the visceral sensitivity to pain in rats.

Visceral pain leads to visceral reactions which manifest themselves, inter alia, by contractions of the abdominal muscles. The number of contractions of the abdominal muscles occurring after a mechanical pain stimulus caused by distending the large intestine is thus a measurement for determining the visceral sensitivity to pain.

The inhibiting activity of the test substances on distension-induced abdominal contractions was tested in rats. The distension of the large intestine with an introduced balloon was used as the stimulus; the contraction of the abdominal muscles was measured as response. One hour after the sensitising of the large intestine by instillation of dilute acetic acid (0.6%, 1.5 ml), a latex balloon was introduced and inflated to 100 mbar for 10 minutes. During this time, the contractions of the abdominal muscles were counted. 20 minutes after subcutaneous administration of the test substance, this measurement was repeated. The activity of the test substance was calculated as a percentage reduction in the counted contractions compared with the control. The reductions in the number of abdominal contractions achieved with different doses of the test substance of Example 1 are listed in percentages, relative to the control values (=100%) measured before ingestion of the substance in the following Table 3.

TABLE 3

Influencing of the visceral sensitivity

| Dose of test substance of Example 1 | Reduction in the number of distension-induced contractions of the abdominal muscles in % relative to control value = 100% |
|---|---|
| 10 μmole/kg | 33% |
| 21.5 μmole/kg | 39% |
| 100 μmole/kg | 61% |

The reduction, achieved by the test substance, in the number of abdominal contractions induced by distension stimulus is a clear indicator of the effectiveness of the test substances with respect to visceral sensitivity to pain.

The foregoing pharmacological test results show that the compounds of Formula I are capable of preventing the disturbances in colon motility caused by stimulation of the afferent nerves, and therefore are suitable for the treatment of IBS. The doses to be used may vary individually and will naturally vary according to the type of condition to be treated and the substance used. In general, however, medicinal forms with an active substance content of 0.1 to 80 mg, in particular 1 to 10 mg, active substance per individual dose are suitable for administration to humans and larger mammals.

In accordance with the invention, the compounds may be contained together with conventional pharmaceutical auxiliaries and/or carriers, in solid or liquid pharmaceutical preparations. Examples of solid preparations include preparations which can be administered orally, such as tablets, coated tablets, capsules, powders or granules, or alternatively suppositories. These preparations may contain conventional pharmaceutical inorganic and/or organic carriers, e.g. talcum, lactose or starch, in addition to conventional pharmaceutical auxiliaries, for example lubricants or tablet disintegrating agents. Liquid preparations such as suspensions or emulsions of the active substances may contain the usual diluents such as water, oils and/or suspension agents such as polyethylene glycols and the like. Other auxiliaries may additionally be added, such as preservatives, taste correctives and the like.

The active substances can be mixed and formulated with the pharmaceutical auxiliaries and/or carriers in a known manner. In order to produce solid medicament forms, the active substances can for example be mixed with the auxiliaries and/or carriers in conventional manner and can be wet or dry granulated. The granules or powder can be poured directly into capsules or be pressed into tablet cores in conventional manner. These can be coated in known manner if desired.

The following examples are intended to illustrate the invention in greater detail, without restricting its scope. The structures of the novel compounds were established partially by spectroscopic investigations, in particular by analysis of the mass or IR spectra, and optionally by determining the optical rotations.

EXAMPLE 1

1-(3,5-bistrifluoromethylbenzoyl)-4-{[3-[N-(2-methoxybenzyl)-N-methyl]amino]propylcarbonyl}-7-phenyl-1,4-diazepane A) 13.5 g 2-methoxybenzaldehyde and 3.5 ml triethylamine were added to 10.3 g 4-aminobutyric acid in 300 ml methanol, and the mixture was hydrogenated in the presence of 10 g Raney nickel at 2 bar. Once the reaction was complete, 12.6 ml of a 37% aqueous formaldehyde solution and 11.4 ml triethylamine were added. After the addition of a further 5 g Raney nickel, hydrogenation was effected again until the hydrogen uptake ended. Then the catalyst was filtered out from the mixture, and the mixture was reduced in volume under vacuum. The [N-methyl-N-(2-methoxybenzyl)]-4-aminobutyric acid triethylamine salt obtained as crude product was used for the next synthesis stage without further purification.

B) 30 g ethylenediamine were added to 96 g ethyl benzoylacetate in 200 ml pyridine and the mixture was boiled under reflux for five hours. Then the pyridine was distilled off and the residue was heated to 180° C. for one hour. After cooling, 500 ml of dichloromethane were added, and the reaction mixture was heated to 40° C. until dissolution occurred. Precipitation with acetone yielded 21.7 g 7-phenyl-1,2,3,4-tetrahydro-1,4-diazepin-5-one having a melting point of 206–214° C.

C) 8.0 g 10% palladium catalyst on activated carbon, suspended in 100 ml ethanol were added to 70 g of the diazepinone obtained above in 300 ml methanol, and then the mixture was hydrogenated at 5 bar in a shaking apparatus. Once the hydrogen uptake had ended, the catalyst was filtered out, and the filtrate was reduced to dryness under vacuum. The residue was taken up in ether; n-hexane was added thereto until clouding occurred, and the mixture was left to stand in a refrigerator overnight. Crystals which formed were filtered out, and in order to complete the crystallization the mother liquor was reduced under vacuum and n-hexane was added thereto. Washing the combined solids fractions with n-hexane and drying yielded 70.3 g of hexahydro-7-phenyl-1,4-diazepin-5-one having a melting point of 85–86° C.

D) 2.0 g LiAlH$_4$ were suspended in THF under a nitrogen atmosphere, and then 5.0 g hexahydro-7-phenyl-1,4-diazepin-5-one were added thereto at 10° C. Then the mixture was stirred for 8 hours at room temperature. Under a nitrogen atmosphere, 5 ml water, 2.2 g NaOH, dissolved in 5 ml water, and again 3 ml water were then added dropwise in succession, and the mixture was stirred for 15 minutes at room temperature. Once the resulting salts had been filtered out, the filtrate was reduced to dryness under vacuum. 4.9 g of 7-phenyl-1,4-diazepane were obtained, which was reacted without further purification.

E) 2.2 g hydroxybenzotriazole in 50 ml DMF, 2.7 g diisopropylcarbodiimide and 2.49 g of the diazepane obtained above under D) in 20 ml dichloromethane were added in succession to a solution of 4.8 g of the crude triethylamine salt obtained above under A) in 50 ml dichloromethane, and the mixture was stirred overnight at room temperature. The solvent was distilled off in a vacuum and the residue was taken up in 100 ml dichloromethane. After the addition of 50 ml of a 10% aqueous tartaric acid solution, the mixture was shaken and the organic phase discarded. The aqueous phase was rendered alkaline with NaOH, and extracted three times with dichloromethane. The combined organic phases were dried over sodium sulfate, filtered and reduced under vacuum. 5.8 g 4-{[[N-(2-methoxybenzyl)-N-methyl]-amino]propylcarbonyl}-7-phenyl-1,4-diazepane were obtained as crude product, which was reacted further without purification.

F) 5.8 g of the diazepane obtained above were dissolved in 50 ml dichloromethane, 3.0 g triethylamine and 4.06 g 3,5-bis-(trifluoromethyl)benzoyl chloride were added thereto in succession at 0° C., and the mixture was stirred for 8 hours at room temperature. The solution was shaken out once with 10% aqueous tartaric acid solution and then once with 10% aqueous sodium hydroxide solution. The combined organic phases were dried over sodium sulfate, filtered and reduced in volume under vacuum. Then the crude product was purified by chromatography on silica gel (mobile solvent: dichloromethane/methanol). 4.5 g of the title compound were obtained, which was converted into the hydrochloride by means of a methanolic HCl solution. Yield: 4.08 g; IR: 3030, 2940, 1635 cm$^{-1}$ (KBr); M$^+$: 635.

EXAMPLE 2

(−)-1-(3,5-bistrifluoromethylbenzoyl)-4-{[3-[N-(2-methoxybenzyl)-N-methyl]amino]propylcarbonyl}-7-phenyl-1,4-diazepane A) 178.2 g hexahydro-7-phenyl-1,4-diazepin-5-one (for preparation see Example 1C) were dissolved in 400 ml methanol and 200 ml isopropanol; a solution of 108.7 g (1S)-(+)-10-camphorsulfonic acid in 800 ml isopropanol was added thereto at 60° C., and the mixture was allowed to stand overnight at room temperature for crystallization. The supernatant solution was decanted, and the crystals were washed twice with 100 ml portions of isopropanol. For recrystallization, the crystals were dissolved at 60° C. in 500 ml methanol, and then 600 ml isopropanol were added thereto. The mixture was allowed to stand overnight, and the mother liquor was decanted off.

The recrystallization was repeated a total of seven times, with the quantities of solvent being reduced to 300 ml methanol and 500 ml isopropanol in each case from the fifth recrystallization onwards. 26.2 g of the camphor sulfonate of the starting compound were obtained, with an optical rotation of $[\alpha]_D^{20}$=+48.1° (c=1.0 in MeOH). The camphor sulfonate was dissolved in 300 ml water and was adjusted to pH 10 using 10% sodium hydroxide solution. After the addition of approximately 50 g common salt, extraction with dichloromethane was performed. The combined organic phases were dried over sodium sulfate, filtered and reduced in volume under vacuum. 9.8 g (+)-hexahydro-7-phenyl-1,4-diazepin-5-one were obtained, $[\alpha]_D^{20}$=+13.1° (c=1.0 in MeOH).

B) 9.0 g of the (+)-diazepinone obtained above were reacted with 3.6 g LiAlH$_4$ analogously to the method given in Example 1D). 8.7 g 7-phenyl-1,4-diazepane were obtained, which were reacted further without purification. A small portion of the diazepane was converted into the hydrochloride by treatment with a solution of HCl in toluene in order to determine the optical rotation, $[\alpha]_D^{20}$=−46.7° (c=1.0 in MeOH).

C) 8.7 g of the diazepane obtained above were reacted with 16.8 g [N-methyl-N-(2-methoxybenzyl)]-4-aminobutyric acid triethylamine salt (for preparation see Example 1A)) using the method given in Example 1E). 20.8 g of an enantiomer of 4-{[[N-(2-methoxybenzyl)-N-methyl]-amino]propylcarbonyl}-7-phenyl-1,4-diazepane were obtained as a crude product, which was reacted without further purification.

D) 20.8 g of the enantiomerically pure diazepane obtained above were reacted with 14.6 g 3,5-bistrifluoromethylbenzoyl chloride according to the method given in Example 1F). 9.9 g of the title compound were obtained, having the optical rotation $[\alpha]_D^{20}$=−33.7° (c=1.0 in MeOH). The crystalline hydrochloride of the title compound was obtained by adding HCl in toluene, melting point=96–101° C., $[\alpha]_D^{20}$=−36.5° (c=1.0 in MeOH).

EXAMPLE 3

1-(3,5-bistrifluoromethylbenzoyl)-4-{[[N-(2-phenylethyl)-N-methyl]amino]acetyl}-7-(2-fluorophenyl)-1,4-diazepane A) 25.2 g malonic acid and 37.3 g ammonium acetate were added to 30.0 g 2-fluorobenzaldehyde in 250 ml ethanol and the mixture was heated to boiling under reflux for 8 hours. Once the mixture had been cooled, the crystals were filtered out, first washed with ethanol and then with a mixture of ethanol and water (75:25 v/v) and dried at 65° C. in a vacuum. 16.5 g DL-3-amino-3-(2-fluorophenyl)-aminopropionic acid were obtained, melting point=229–231° C.

B) 10.0 g of the propionic acid obtained above were dissolved in a mixture of 200 ml THF and 50 ml water, and 7.7 g benzoyl chloride in 30 ml THF and 10% sodium hydroxide solution were added thereto dropwise alternately with ice cooling, so that the pH value was maintained at approximately 10. Once the addition had ended, stirring was effected for about 15 minutes at room temperature. Then the solvent was distilled off under vacuum, and the remaining aqueous phase was adjusted to pH 1 with dilute aqueous hydrochloric acid solution. The resulting crystals were filtered out, washed with acetone and dried under vacuum. 15.4 g N-benzoyl-3-amino-3-(2-fluorophenyl)-propionic acid having a melting point of 202–205° C. were obtained.

C) 10.0 g of the benzoylated propionic acid obtained above were dissolved in 100 ml dichloromethane; 5.8 ml triethylamine were added thereto, and then the mixture was cooled to −10° C. Then 3.32 ml ethyl chloroformate were added dropwise, and the reaction mixture was stirred for a further 30 minutes at −10° C. Then 3.81 ml benzylamine were added dropwise, and the solution was stirred for one hour at room temperature. The solvent was removed under vacuum, and the residue was taken up in ethyl acetate and water and shaken. The organic phase was reduced in volume under vacuum, and the mixture was then allowed to stand for crystallization. The resulting crystals were washed with acetone and dried under vacuum. 10.6 g N-benzoyl-3-amino-3-(2-fluorophenyl)-propionic acid benzylamide were obtained, melting point=223–226° C.

D) 5.0 g LiAlH$_4$ were suspended in a mixture of toluene and THF (70:30 v/v), and 10.5 g of the benzylamide obtained above were added thereto in portions under a protective gas atmosphere. Then the mixture was boiled for 8 hours under reflux, cooled to 0° C., and 20 ml THF, 10 ml water and 50 ml 10% sodium hydroxide solution were added dropwise thereto in succession under nitrogen. The batch was filtered, the salts which separated were washed with ethanol, and the combined liquid phases were evaporated to dryness in a vacuum. The residue was taken up in a little dichloromethane and filtered with dichloromethane over magnesium silicate (for chromatography). The product, obtained as an oil, was dissolved in 50 ml dichloromethane, an excess of hydrochloric acid dissolved in isopropanol was added thereto in order to form a salt, and the product was crystallized out by adding diethyl ether. The crystals were filtered out and washed with diethyl ether. 8.96 g of 1-(2-fluorophenyl)-1,3-(N,N'-dibenzyl)-diaminopropane were obtained as a dihydrochloride having a melting point of 195–198° C.

E) 3.09 g 40% aqueous glyoxal solution and then 4.68 g sodium cyanoborohydride were added in portions to 8.96 g of the dihydrochloride obtained above in 70 ml methanol at 10° C., and the mixture was stirred for 18 hours at room temperature. Then the mixture was evaporated under a vacuum, the residue was taken up in dichloromethane and ethanol (90:10 v/v) and purified first in this solvent mixture as mobile solvent over silica gel, then in dichloromethane/n-hexane as mobile solvent over aluminium oxide. 3.91 g 7-(2-fluorophenyl)-(N,N'-dibenzyl)-1,4-diazepane were obtained, which was recrystallized from ether/n-hexane, melting point=82–83° C.

F) 4.03 g 1-chloroethyl chloroformate were added dropwise to 10.0 g of the diazepane obtained above in 50 ml 1,2-dichloroethane at 0° C., and then the mixture was boiled under reflux for 2 hours. The mixture was reduced to approximately ⅓ of its volume under a vacuum; 30 ml methanol were added thereto, and the mixture was again heated to boiling for 3 hours under reflux. Then the mixture was evaporated to dryness under a vacuum, and the residue was taken up in 10 ml dichloromethane and chromatographed over silica gel (mobile solvent: dichloromethane/methanol). 5.89 g 1-benzyl-7-(2-fluorophenyl)-1,4-diazepane were obtained, which was used for the next synthesis stage without further purification.

G) 2.3 ml diisopropylethylamine and 0.87 ml chloracetyl chloride were added in succession to 3.10 g of the monobenzyldiazepane obtained above in 20 ml dichloromethane at 0° C., and the mixture was stirred for 3 hours. Then the solution was chromatographed over silica gel (mobile solvent: dichloromethane/methanol 98:2). Once the solvent had been evaporated off, 2.44 g 1-benzyl-4-chloracetyl-7-(2-fluorophenyl-1,4)-diazepane were obtained as an oil, which was used for the next synthesis stage without further purification or characterization.

H) 0.85 ml diisopropylethylamine and 0.54 g N-methylphenylethylamine were added to 1.43 g of the 4-chloracetyl-1,4-diazepane obtained above in 20 ml methanol, and the mixture was then heated to its boiling point for 5 hours under reflux. Then the mixture was evaporated under a vacuum, and the residue was taken up in 5 ml dichloromethane and purified by chromatography on silica gel (mobile solvent dichloromethane/methanol). Then the isolated crude product was dissolved in 20 ml diethyl ether, and an excess of methanolic hydrochloric acid solution was added thereto. The mixture was reduced in volume, and the residue taken up in a little dichloromethane. After the addition of a few drops of a solution of hydrochloric acid in a mixture of isopropanol and diethyl ether, the 1-benzyl-4-{[[N-phenylethyl-N-methyl]amino]acetyl}-7-(2-fluorophenyl)-1,4-diazepane crystallized out as a hydrochloride. 0.26 g of crystals were obtained, having a melting point of 141–143° C.

I) 2 ml 2-normal aqueous hydrochloric acid solution and 0.3 g 5% palladium catalyst on activated carbon were added to 0.95 g of the diazepane compound obtained above in 20 ml ethanol, and the mixture was hydrogenated for 5 hours at room temperature. Then the catalyst was filtered out, and the solution was evaporated under a vacuum. Then 2 ml of 10% sodium hydroxide solution and 30 ml dichloromethane were added, and the mixture was shaken. The organic phase was separated, dried over sodium sulfate, reduced to about 10 ml under a vacuum and chromatographed over silica gel (mobile solvent: dichloromethane/methanol). 0.52 g of 4-{[[N-phenylethyl-N-methyl]-amino]acetyl}-7-(2-fluorophenyl)-1,4-diazepane were obtained as an oil, which was used for the next synthesis stage without further purification or characterization.

J) 0.52 g of the oily debenzylated diazepane compound obtained above were reacted in the manner given in Example 1F) with 0.75 g diisopropylethylamine and 0.39 g of 3,5-bis-(trifluoromethyl)benzoyl chloride. 0.82 g of an oily crude product were obtained, which was taken up in 50 ml diethyl ether and to which a solution of 0.16 g maleic acid in 5 ml THF was added. The resulting mixture was reduced to approximately 10 ml and was placed in a refrigerator to crystallize. 0.7 g of the title compound were obtained as maleinate having a melting point of 156–158° C.

EXAMPLE 4

1-(3,5-dimethylbenzoyl)-4-{[N-(2-methoxybenzyl) amino]acetyl}-7-phenyl-1,4-diazepane A) 1.9 g hexahydro-7-phenyl-1,4-diazepin-5-one (for preparation see Example 1C) in 30 ml acetonitrile were heated to boiling with 2.0 g potassium carbonate and 1.2 g benzyl chloride with reflux cooling for 36 hours. Then filtration was carried out and the filtrate reduced in volume. The remaining residue was shaken with 10% aqueous citric acid solution, the organic phase was separated, dried over magnesium sulfate and reduced in volume under a vacuum. 2.23 g crude 1-benzyl-hexahydro-7-phenyl-1,4-diazepin-5-one were obtained as an oil, which was used for the next synthesis stage without further purification or characterization.

B) 2.2 g of the benzylated diazepinone obtained above were reduced in the manner described in Example 3D) with 0.8 g LiAlH$_4$. 1.64 g 1-benzyl-7-phenyl-1,4-diazepane were obtained as an oil, which was reacted without further purification or characterization.

C) 1.46 g of the benzylated diazepane compound obtained above, 1.10 g N-(3-dimethylaminopropyl)-N'-ethyl carbodiimide and 0.96 g tert.butoxycarbonylglycine were dissolved in 30 ml dichloromethane and stirred for 5 hours at room temperature. The mixture was shaken with 10% aqueous citric acid solution, then the organic phase was separated and dried over magnesium sulfate. Removal of the solvent under a vacuum yielded 2.76 g crude 1-benzyl-4-{[N-(tert.butoxycarbonyl)amino]acetyl}-7-phenyl-1,4-diazepane, which was reacted without further purification.

D) 1.0 g 20% palladium hydroxide catalyst on activated carbon were mixed with 2.5 g of the monoacylated diazepane derivative obtained above in 100 ml ethanol, and the mixture was hydrogenated for 4 hours. Once the catalyst had been filtered out, the filtrate was reduced in volume; shaken with 15% aqueous tartaric acid solution, and the aqueous phase was extracted with 10% aqueous sodium hydroxide solution. Separation of the organic phase, drying over magnesium sulfate and concentration in a vacuum yielded 1.78 g 4-[N-(tert.butoxycarbonyl)amino]acetyl}-7-phenyl-1,4-diazepane, IR: 1700 cm$^{-1}$.

E) 1.7 g of the debenzylated diazepane obtained above were reacted with 1.0 g triethylamine and 0.86 g 3,5-dimethylbenzoyl chloride in the manner described in Example 1F). 2.42 g 1-(3,5-dimethylbenzoyl)-4-{[N-tert.butoxycarbonyl]amino]acetyl}-7-phenyl-1,4-diazepane were obtained as a foam resin, which was reacted without further purification or characterization.

F) 10 ml trifluoroacetic acid were added to 2.08 g of the bisacylated diazepane obtained above in 100 ml dichloromethane and stirred overnight at room temperature. Then the mixture was reduced in volume under a vacuum, and the residue was taken up in 100 ml dichloromethane and shaken three times with 1-normal sodium hydroxide solution. The organic phase was separated, dried over sodium sulfate and reduced in volume under a vacuum. 1.5 g of crude 1-(3,5-dimethylbenzoyl)-4-aminoacetyl-1,4-diazepane were obtained, which was reacted without further purification or characterization.

G) 0.8 g of the diazepane compound prepared above were dissolved in 100 ml ethanol, and 0.3 g 2-methoxybenzaldehyde and a spatula-tip of Raney nickel were added thereto in succession. Then hydrogenation was effected at 3 bar and room temperature. Once the hydrogen uptake had ended, the catalyst was filtered out, and the filtrate was concentrated in a vacuum. The residue was chromatographed on silica gel (mobile solvent: dichloromethane/methanol), with 0.3 g of the title compound being obtained: IR: 3030, 2940, 1635 cm$^{-1}$; M$^+$: 485.

EXAMPLE 5

1-(3,5-bistrifluoromethylbenzoyl)-4-{[3-[N-(3-phenylpropyl)amino]propyl]amino-carbonyl}-7-phenyl-1,4-diazepane A) 0.8 g sodium hydroxide, 10 ml water and 4.36 g di-tert.butyl dicarbonate were added to 1.78 g β-alanine in 30 ml THF, and the mixture was stirred for 60 hours at room temperature. Then the mixture was reduced in volume under a vacuum, and the residue was taken up in dichloromethane and shaken with 10% aqueous tartaric acid solution. The organic phase was separated, dried over sodium sulfate, filtered and concentrated in a vacuum. 3.35 g crude N-tert.butoxycarbonyl-β-alanine were obtained, which was reacted further without purification.

B) 3.5 g triethylamine, 4.8 g 2-chloro-1-methylpyridinium iodide and 2.13 g 3-phenyl-1-aminopropane were added to 3.0 g of the N-protected β-alanine prepared above in 30 ml dichloromethane, and the mixture was stirred for 18 hours at room temperature. Then the reaction mixture was shaken with 15% aqueous tartaric acid solution, after which the organic phase was separated and dried over sodium sulfate. After filtration and volume reduction, chromatography was carried out on silica gel (mobile solvent dichloromethane/methanol 99:1). 3.41 g N-tert.butoxycarbonyl-C-[(3-phenylpropyl)amino]-β-alanine were obtained, which was reacted further unpurified.

C) 23.7 g of the BOC-protected compound prepared above were reduced with 8.0 g LiAlH$_4$ according to the method described in Example 3D). 17.7 g oily 1-[N-(tert.butoxycarbonyl)amino]-3-[N-(3-phenylpropyl)amino]-1,3-diaminopropane were obtained, which was reacted further without purification.

D) 3.76 g of the diaminopropane derivative obtained above were dissolved in 50 ml THF, and a total of 13 ml 1N sodium hydroxide solution and 2.4 g benzyloxycarbonyl chloride were added thereto alternately in portions at 10° C. Once reaction was completed, the aqueous phase was separated and extracted twice with 50 ml portions of dichloromethane. The combined organic phases were dried over sodium sulfate and reduced in volume under a vacuum. Chromatography on silica gel (mobile solvent: dichloromethane/methanol) yielded 1-[N-tert.butoxycarbonyl-amino]-3-{[N-(3-phenylpropyl)-N-benzyloxycarbonyl)-amino}-1,3-diaminopropane as intermediate product, which was dissolved in 70 ml acetonitrile and to which 2.4 g p-toluenesulfonic acid was added. This mixture was stirred for 18 hours at room temperature, and then was reduced in volume under a vacuum. 20 ml 1-normal sodium hydroxide solution was added to the residue, and the mixture was extracted 3 times with 30 ml portions of dichloromethane. The combined organic phases were dried over sodium sulfate, filtered and reduced in volume under a vacuum. Chromatography of the residue on silica gel (mobile solvent: dichloromethane/methanol) yielded 3.4 g oily 1-amino-3-[N-(3-phenylpropyl)-N-benzyloxycarbonyl]amino-1,3-diaminopropane, which was reacted further without purification.

E) 16.4 g hexahydro-7-phenyl-1,4-diazepan-5-one (for preparation see Example 1C)) in 100 ml THF were reacted with 25.5 ml 3-normal sodium hydroxide solution and 19.0 g di-tert.butyl dicarbonate in accordance with the method described above under A). 23.4 g 1-tert.butoxycarbonyl-hexahydro-7-phenyl-1,4-diazepin-5-one were obtained, which were reacted further without purification.

F) 27.0 g of the BOC-protected diazepinone prepared above were dissolved in THF and were stirred with 14.0 g LiAlH$_4$ for 18 hours at room temperature according to the method described above in Example 3D). Once the resulting salts had been filtered out, the filtrate was reduced in volume under a vacuum and chromatographed twice over silica gel (mobile solvent: THF/MeOH). 6.5 g 1-tert.butoxycarbonyl-7-phenyl-1,4-diazepane were obtained, which was reacted further without purification.

G) 1.77 g of the protected diaminopropane derivative obtained above under D) were dissolved in 50 ml dichloromethane, and 2.1 g diisopropylethylamine and 0.53 g bis-(trichloromethyl)-carbonate ("triphosgene") were added thereto with stirring and ice cooling. Then the reaction mixture was added dropwise with ice cooling to a solution of 1.5 g of the diazepane obtained above under F) in dichloromethane and was stirred for 3 hours at room temperature. The mixture was then shaken with 10% aqueous citric acid solution, then the organic phase was separated, dried over sodium sulfate, filtered and concentrated in a vacuum. Chromatography on silica gel (mobile solvent: THF/MeOH) yielded 2.88 g 1-tert.butoxycarbonyl-4-{[3-[N-(3-phenylpropyl)-N-benzyloxycarbonyl]amino]propyl]aminocarbonyl}-7-phenyl-1,4-diazepane as an oily crude product, which was reacted without further purification.

H) 3.8 g of the diazepane compound obtained above were dissolved in 50 ml acetonitrile; 2.5 g p-toluenesulfonic acid were added thereto, and the mixture was stirred for 18 hours at room temperature. Then the reaction mixture was reduced in volume under a vacuum, and the residue was chromatographed over silica gel (mobile solvent: dichloromethane/methanol 90:10). The combined fractions yielded 1.83 g oily 4-{[3-[N-(3-phenylpropyl)-N-benzyloxycarbonyl]-aminopropyl]aminocarbonyl}-7-phenyl-1,4-diazepane, which was reacted without further purification.

I) Of the 1-N deprotected diazepane compound obtained above, 1.8 g were dissolved in dichloromethane and were reacted with 0.35 g triethylamine and 1.0 g 3,5-bistrifluoromethylbenzoyl chloride according to the method described above in Example 1H). After two filtrations over silica gel at elevated pressure (mobile solvent for first filtration: dichloromethane, mobile solvent for second filtration: dichloromethane/MeOH 98:2), 1.66 g of amorphous 1-(3,5-bis-trifluoromethylbenzoyl)-4-{[3-[N-(3-phenylpropyl)-N-benzyloxycarbonyl]aminopropyl]aminocarbonyl}-7-phenyl-1,4-diazepane were obtained, IR: 3010, 1680, 1630 cm$^{-1}$; M$^+$: 755.

J) 1.66 g of the coupling product obtained above were dissolved in 100 ml ethanol; 0.5 g 10% palladium catalyst on activated carbon were added thereto, and the mixture was hydrogenated until the hydrogen uptake had ended. Then the catalyst was filtered out, and the filtrate was reduced in volume under a vacuum. The residue was chromatographed over silica gel (mobile solvent: THF/MeOH). 0.61 g of the title compound were obtained, IR: 3420, 2920, 1630 cm$^-$; M$^+$: 621.

EXAMPLE 6

1-(3,5-dimethylbenzoyl)-4-{2-[(N-benzyl-N-methyl)aminoethyl]}aminocarbonyl-7-phenyl-1,4-diazepane A) 3.0 g hexahydro-7-phenyl-1,4-diazepin-5-one (for preparation see Example 1C)) in 40 ml dichloromethane were reacted with 4.0 g triethylamine and 2.9 g 3,5-dimethylbenzoyl chloride according to the method given above in Example 1F). 5.01 g amorphous 1-(3,5-dimethylbenzoyl)-hexahydro-7-phenyl-1,4-diazepin-5-one were obtained, which was reacted without further purification.

B) 2.28 g triethyloxonium tetrafluoroborate were added to 3.52 g of the diazepinone compound prepared above in 50 ml dichloromethane, and the mixture was stirred for 1.5 hours at room temperature. Then the solution was reduced in a vacuum, and the residue was taken up in 50 ml ethanol. Then 0.9 g sodium borohydride were added in portions, and the mixture was stirred for 18 hours at room temperature. Then the solvent was removed under a vacuum, and the residue was taken up with a mixture of dichloromethane and water and shaken. The organic phase was separated, dried over sodium sulfate, filtered and evaporated in a vacuum. Chromatography on silica gel (mobile solvent: toluene/methanol) yielded 2.3 g of 1-(3,5-dimethylbenzoyl)-7-phenyl-1,4-diazepane, which was reacted without further purification.

C) 1.76 g of the reduced product prepared above were dissolved in 50 ml dichloromethane; 0.6 g chloroethyl isocyanate were added thereto, and the mixture was stirred for 2 hours at room temperature. After the addition of toluene, the mixture was reduced in volume to dryness under a vacuum, and the resulting 1-(3,5-dimethylbenzoyl)-4-[(2-chloroethyl)aminocarbonyl]-7-phenyl-1,4-diazepane] was processed further as a crude product.

D) 2.3 g of the chloroethylurea compound obtained above were dissolved in 80 ml acetonitrile and were heated to boiling under reflux with 1.0 g diisopropylethylamine and 0.7 g N-methylbenzylamine for 18 hours. Then the solution was reduced in volume under a vacuum and taken up with methyl tert.butyl ether. The mixture was shaken with 50 ml 10% aqueous tartaric acid solution, and the aqueous phase was extracted three times with dichloromethane. The combined organic phases were dried over sodium sulfate, filtered and evaporated in a vacuum. Chromatography on silica gel (mobile solvent: dichloromethane/methanol) yielded 0.56 g of the title compound, IR: 3015, 2920, 1630 cm$^{-1}$; M$^+$: 498.

EXAMPLE 7

1-(3,5-bistrifluoromethylbenzoyl)-4-[3-(N-benzyl-N-methyl)aminopropyl]-aminocarbonyl-7-phenyl-1,4-diazepane A) 12.2 g N-methylbenzylamine were dissolved in 100 ml dichloromethane; 6.4 g acrylonitrile was added thereto, and the mixture was stirred for 10 minutes at room temperature. Five drops of a 40% solution of benzyltrimethylammonium hydroxide in methanol were added as catalyst, and the mixture was then stirred for 6 hours at room temperature. Then the solution was extracted once with 100 ml dilute aqueous acetic acid, and the organic phase was separated and dried over sodium sulfate. The drying agent was filtered out and the solvent was removed under a vacuum. Then the residue was chromatographed over silica gel (mobile solvent: initially n-hexane/dichloromethane, to which increasing portions of dichloromethane up to 100% were added). 10.4 g 3-(N-methyl-N-benzyl)aminopropionitrile were obtained, which was reacted without further purification or characterization.

E) The propionitrile obtained above was dissolved in 200 ml methanol; 50 ml concentrated aqueous ammonia solution and 200 mg Raney nickel were added thereto in succession, and then hydrogenation was effected at room temperature and 2 bar pressure. Once the hydrogen uptake had ended, the catalyst was filtered out, and the filtrate was reduced in volume under a vacuum. The resulting 1-[(N-methyl-N-benzyl)amino]-1,3-diaminopropane was used for the next synthesis stage without further purification.

C) 17.2 g hexahydro-7-phenyl-1,4-diazepin-5-one (for preparation see Example 1C)) in 300 ml dichloromethane were reacted with 15.0 g triethylamine and 25.0 g 3,5-bistrifluoromethylbenzoyl chloride according to the method given above in Example 1F). 36.6 g 1-(3,5-bistrifluoromethyl)-hexahydro-7-phenyl-1,4-diazepin-5-one were obtained, melting point=169–171° C.

D) 2.1 g of the diazepinone compound prepared above, 1.2 g triethyloxonium tetrafluoroborate and 0.5 g sodium borohydride were reacted in the manner given above in Example 6B). 1.3 g 1-(3,5-bistrifluoromethylbenzoyl)-7-phenyl-1,4-diazepane having a melting point of 151–153° C. were obtained.

E) 0.36 g of the diaminopropane obtained above under B) were dissolved in 20 ml dichloromethane, and 0.3 ml triethylamine and 1 ml of a 20% solution of phosgene in toluene were added thereto in succession. The mixture was stirred for 2 hours at room temperature and then reduced in volume under a vacuum. The residue was dissolved in 20 ml dichloromethane, and a solution of 0.6 g of the 1-(3,5-bistrifluoromethylbenzoyl)-7-phenyl-1,4-diazepane obtained above and 1 ml triethylamine in 20 ml dichloromethane was added dropwise to this solution at room temperature. Then stirring was carried out for 2 hours at room temperature, followed by reduction in a vacuum. Chromatography on silica gel (mobile solvent: n-hexane/dichloromethane) yielded 0.11 g of the title compound; IR: 3300, 1630, 1245 cm$^{-1}$ (KBr); M$^+$: 498.

EXAMPLE 8

1-(3,5-bistrifluoromethylbenzoyl)-4-{2-[N-(2-methoxybenzyl)]aminoethyl}-7-phenyl-1,4-diazepane A) 6.6 g triethylamine were added to 10.0 g N-(tert.butoxycarbonyl)glycine in 100 ml dichloromethane. Then 6.2 g ethyl chloroformate in 20 ml dichloromethane were added dropwise at 0° C.; the mixture was stirred for 15 minutes at 0° C., and then a solution of 8.1 g 2-methoxybenzylamine in 25 ml dichloromethane was added thereto dropwise. The mixture was stirred for another 3 hours at room temperature before being extracted once with 100 ml of a 10% aqueous tartaric acid solution. The organic phase was dried over magnesium sulfate, filtered and reduced in volume under a vacuum. 13.9 g N-(tert.butoxycarbonyl)-glycine-(2-methoxybenzyl)amine were obtained, having a melting point of 96–97° C.

B) 2.5 g LiAlH$_4$ were suspended in a mixture of 100 ml each of THF and toluene under a nitrogen atmosphere. 13.9 g of the glycine derivative obtained above, dissolved in 50 ml THF, were slowly added dropwise thereto at room temperature, and the mixture was stirred for 4 hours at room temperature. Then 10 ml water in 150 ml THF and subsequently 40 ml of a 5% aqueous sodium hydroxide solution were added dropwise with ice cooling. The resulting precipitate was filtered out, and the filtrate was reduced in volume under a vacuum. 8.3 g 1-[N-(tert.butoxycarbonyl)]-2-[N-(2-methoxybenzyl)amino]-1,2-diaminoethane were obtained, which was used without further purification for the next synthesis stage.

C) 8.3 g of the diaminoethane obtained above were dissolved in 100 ml THF. With ice cooling, a solution of 4.0 g benzyl chloroformate in 15 ml THF and a solution of 1.0 g sodium hydroxide in 50 ml water were added dropwise thereto via two dropping funnels such that the temperature did not exceed 10° C. and the pH value of the solution was between 9.5 and 10. Once addition had been completed, the reaction mixture was stirred for 2 hours at room temperature. After the addition of 10 g sodium chloride, the organic phase was separated, dried over magnesium sulfate, filtered and reduced in volume under a vacuum. The residue was taken up in dichloromethane and extracted once with 10% aqueous tartaric acid solution. The organic phase was separated again, dried over magnesium sulfate, filtered and reduced in volume under a vacuum. 5.1 g crude 1-[N-(tert.butoxycarbonyl)-2-[N-benzyloxycarbonyl-N-(2-methoxybenzyl)]amino-1,2-diaminoethane were obtained, which was reacted without further purification.

D) 5.0 g of the product obtained above were dissolved in 100 ml acetonitrile, and 4.7 g p-toluenesulfonic acid were added thereto. Then stirring was carried out for 6 hours at room temperature, followed by reduction in volume under a vacuum. The residue was taken up in 50 ml dichloromethane and extracted once with 50 ml water. The organic phase was separated, dried over sodium sulfate and the solvent was removed at reduced pressure. Chromatography on silica gel (mobile solvent: dichloromethane/methanol) yielded 1.9 g 1-[N-benzyloxycarbonyl-N-(2-methoxybenzyl)]-amino-1,2-diaminoethane; IR=3060, 3030, 2960, 1700 cm$^{-1}$ (KBr).

E) 0.31 g of the diaminoethane obtained above were dissolved in 20 ml dichloromethane, and 0.26 g triethylamine and 0.6 ml of a 20% solution of phosgene in toluene were added to this receiving solution in succession at 0° C. Then the mixture was stirred for 2 hours at room temperature, and then reduced in volume under a vacuum. The resulting {2-[N-benzoyloxycarbonyl-N-(2-methoxybenzyl)]amino}ethyl]isocyanate was taken up in 10 ml dichloromethane and used for the next synthesis stage without further purification.

F) The isocyanate solution obtained above was added dropwise to 0.41 g 1-(3,5-bistrifluoromethylbenzoyl)-7-phenyl-1,4-diazepane (for preparation see Example 7D)) in 20 ml dichloromethane at 0° C. and then stirred for 3 hours at room temperature. Then extraction was performed once with 20 ml water, the organic phase was separated, dried over sodium sulfate, filtered and reduced in volume under a vacuum. Chromatography on silica gel (mobile solvent: dichloromethane/methanol) yielded 0.43 g 1-(3,5-bistrifluoromethylbenzoyl)-4-{2-[N-(2-methoxybenzyl)-N-benzyloxycarbonyl]amino}ethylaminocarbonyl-7-phenyl-1,4-diazepane, IR: 3010, 1680, 1630 cm$^{-1}$; M$^+$: 756.

G) The product obtained above was dissolved in 50 ml ethanol, and a spatula-tip of 10% palladium catalyst on activated carbon was added thereto. Then hydrogenation was effected at room temperature and a pressure of 3 bar. After 3 hours, the catalyst was filtered out; the filtrate was reduced in volume under a vacuum, and the residue was chromatographed on silica gel (mobile solvent: dichloromethane/methanol). 0.12 g of the title compound were obtained as oil, IR: 2420, 2920, 1630 cm$^{-1}$; M$^+$: 622.

The compounds of Formula I listed in the following Table A can also be prepared in accordance with the processes described in the foregoing examples.

TABLE A

| Example No. | $R^1$ | $R^2$ | $R^3$ | $R^4$ | $R^5$ | $R^6$ | $R^7$ | A | B | MS [M$^+$] | IR [cm$^{-1}$] |
|---|---|---|---|---|---|---|---|---|---|---|---|
| 9 | H | H | H | H | H | CF$_3$ | CF$_3$ | CH$_2$ | CH(CH$_3$) | 577 | 3020, 1640 |
| 10 | H | 2-OCH$_3$ | H | H | H | CF$_3$ | CF$_3$ | CH$_2$ | CH$_2$ | 593 | 3020, 1640 |
| 11 | | N.N. | | | | | | | | | |
| 12 | H | H | H | H | H | CH$_3$ | CH$_3$ | CH$_2$ | (CH$_2$)$_3$ | 483 | 3020, 1640 |
| 13 | H | H | H | H | H | CF$_3$ | CF$_3$ | CH$_2$ | (CH$_2$)$_3$ | 591 | 3010, 1645 |
| 14 | H | 2-OCH$_3$ | H | H | H | CF$_3$ | CF$_3$ | (CH$_2$)$_3$ | CH$_2$ | 621 | 2920, 1635 |
| 15 | CH$_3$ | 2-OCH$_3$ | H | H | H | CH$_3$ | CH$_3$ | CH$_2$ | CH$_2$ | 499 | 2940, 1635 |
| 16 | CH$_3$ | 2-OCH$_3$ | H | H | H | CF$_3$ | CF$_3$ | CH$_2$ | CH$_2$ | 607 | 3020, 2940, 1640 |
| 17 | CH$_3$ | H | H | H | H | CH$_3$ | CH$_3$ | CH$_2$ | (CH$_2$)$_3$ | 497 | 3010, 1630 |
| 18 | H | 2-OCH$_3$ | H | H | H | CH$_3$ | CH$_3$ | (CH$_2$)$_2$ | CH$_2$ | 499 | 2940, 1630 |
| 19 | CH$_3$ | 2-OCH$_3$ | H | 2-F | H | CF$_3$ | CF$_3$ | (CH$_2$)$_3$ | CH$_2$ | 653 | 2940, 1635 |
| 20 | CH$_3$ | H | H | H | H | CH$_3$ | CH$_3$ | HN—(CH$_2$)$_2$— | CH$_2$ | 498 | 3015, 2910, 1640 |
| 21 | CH$_3$ | 4-F | H | H | H | CF$_3$ | CF$_3$ | (CH$_2$)$_3$ | CH$_2$ | 623 | 3020, 1630 |

M$^+$: Mass of the molecular ion, observed by mass spectrometry
N.N.: Entry not occupied.

EXAMPLE I

Tablets Containing 1-(3,5-bistrifluoromethylbenzoyl)-4-{[3-[N-(2-methoxybenzyl)-N-methyl]amino]propylcarbonyl}-7-phenyl-1,4-diazepane Tablets were produced having the following composition per tablet:

| | |
|---|---|
| 1-(3,5-bistrifluoromethylbenzoyl)-4-{[3-[N-(2-methoxybenzyl)-N-methyl]amino]-propylcarbonyl}-7-phenyl-1,4-diazepane hydrochloride | 20 mg |
| Corn starch | 60 mg |
| Lactose | 135 mg |
| Gelatine (as 10% solution) | 6 mg |

The active compound, the corn starch and the lactose were thickened with the 10% gelatine solution. The paste was ground, and the resulting granules were placed on a suitable tray and dried at 45° C. The dried granules were passed through a crusher and mixed in a mixer with the following additional auxiliaries:

| | |
|---|---|
| Talcum | 5 mg |
| Magnesium stearate | 5 mg |
| Corn starch | 9 mg | and then pressed into 240 mg tablets.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A compound corresponding to the formula I:

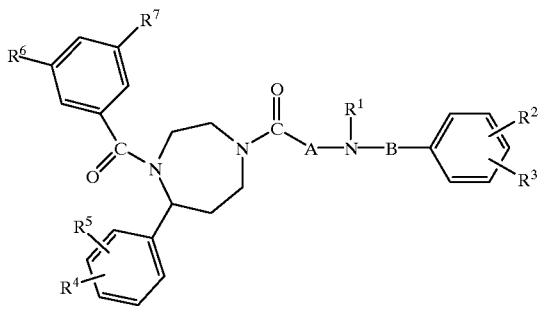

wherein $R^1$ is hydrogen or lower alkyl, $R^2$ is hydrogen, lower alkyl, lower alkoxy, halogen or trifluoromethyl, and $R^3$ is hydrogen, lower alkyl, lower alkoxy, halogen or trifluoromethyl, or $R^2$ and $R^3$ together are alkylenedioxy with 1 to 2 carbon atoms, bonded to adjacent carbon atoms of the phenyl ring, $R^4$ is hydrogen, lower alkyl, lower alkoxy, halogen or trifluoromethyl, and $R^5$ is hydrogen, lower alkyl, lower alkoxy, halogen or trifluoromethyl, or $R^4$ and $R^5$ together are alkylenedioxy with 1 to 2 carbon atoms, bonded to adjacent carbon atoms of the phenyl ring, $R^6$ is lower alkyl, halogen or trifluoromethyl, $R^7$ is lower alkyl, halogen or trifluoromethyl, A is a —$(CH_2)_n$— group in which n represents an integer from 1 to 3, or an —NH—$(CH_2)_m$— group in which m represents an integer from 2 to 3, and B is an alkylene chain with 1 to 3 carbon atoms, optionally substituted by lower alkyl, or a pharmaceutically acceptable acid addition salt thereof.

2. A compound according to claim 1, wherein at least one of $R^6$ and $R^7$ is trifluoromethyl.

3. A compound according to claim 1, wherein $R^2$ is hydrogen, and $R^3$ represents 2-methoxy.

4. 1-(3,5-bistrifluoromethylbenzoyl)-4-{3-[N-(2-methoxybenzyl)-N-methylamino]-propylcarbonyl}-7-phenyl-1,4-diazepane according to claim 3 or a pharmaceutically acceptable acid addition salt thereof.

5. A pharmaceutical composition comprising a pharmacologically effective quantity of a compound according to claim 1, and at least one pharmaceutical carrier or adjuvant.

6. A process for preparing a compound corresponding to the formula I:

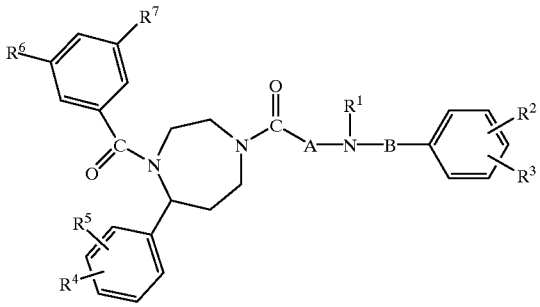

wherein $R^1$ is hydrogen or lower alkyl, $R^2$ is hydrogen, lower alkyl, lower alkoxy, halogen or trifluoromethyl, and $R^3$ is hydrogen, lower alkyl, lower alkoxy, halogen or trifluoromethyl, or $R^2$ and $R^3$ together are alkylenedioxy with 1 to 2 carbon atoms, bonded to adjacent carbon atoms of the phenyl ring, $R^4$ is hydrogen, lower alkyl, lower alkoxy, halogen or trifluoromethyl, and $R^5$ is hydrogen, lower alkyl, lower alkoxy, halogen or trifluoromethyl, or $R^4$ and $R^5$ together are alkylenedioxy with 1 to 2 carbon atoms, bonded to adjacent carbon atoms of the phenyl ring, $R^6$ is lower alkyl, halogen or trifluoromethyl, $R^7$ is lower alkyl, halogen or trifluoromethyl, A is a —$(CH_2)_n$— group in which n represents an integer from 1 to 3, or an —NH—$(CH_2)_m$— group in which m represents an integer from 2 to 3, and B is an alkylene chain with 1 to 3 carbon atoms, optionally substituted by lower alkyl, or a pharmaceutically acceptable acid addition salt thereof, said process comprising the steps of:

a) to prepare a compound of Formula I, reacting a compound of formula IIa:

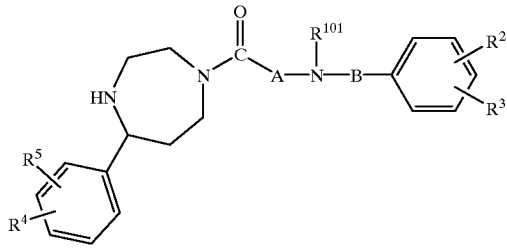

wherein $R^2$, $R^3$, $R^4$, $R^5$, A and B have the above meanings and $R^{101}$ represents lower alkyl or an amino protective group, with a compound of formula III:

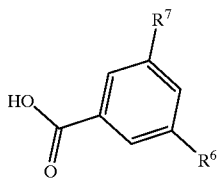

wherein $R^6$ and $R^7$ have the above meanings, and cleaving off any amino protective group $R^{101}$, or b) to prepare a compound of formula Ia,

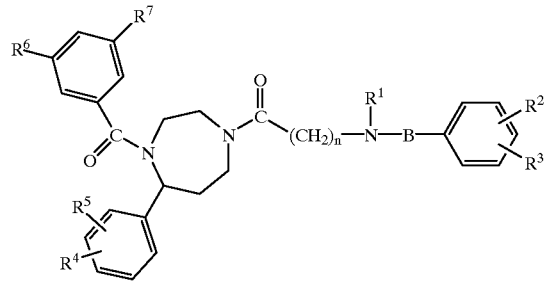

wherein $R^1$, $R^2$, $R^3$, $R^4$, $R^5$, $R^6$, $R^7$, B and n have the above meanings, reacting a compound of formula IV:

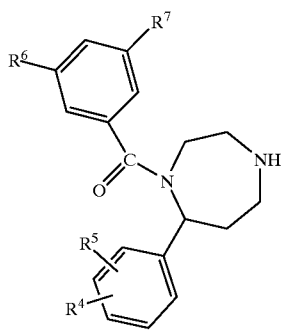

wherein $R^4$, $R^5$, $R^6$ and $R^7$ have the above meanings, with a compound of formula V:

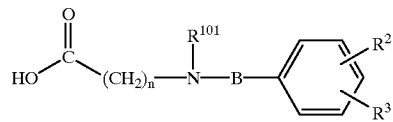

wherein $R^{101}$, $R^2$, $R^3$, B and n have the above meanings, and cleaving off any amino protective group $R^{101}$, or c) to prepare a compound of formula Ib:

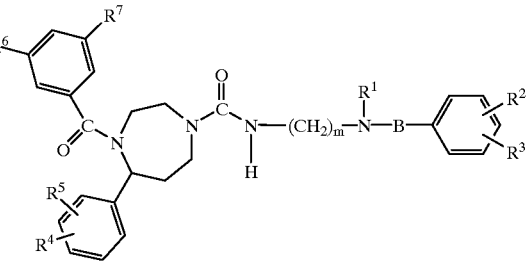

wherein $R^1$, $R^2$, $R^3$, $R^4$, $R^5$, $R^6$, $R^7$, B and m have the above meanings, reacting a compound of Formula IV with a compound of formula VI,

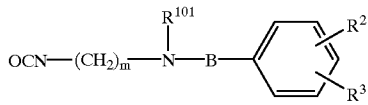

wherein $R^{101}$, $R^2$, $R^3$, B and m have the above meanings, and cleaving off any amino protective group $R^{101}$, or d) to prepare a compound of Formula I, reacting a compound of formula VIII:

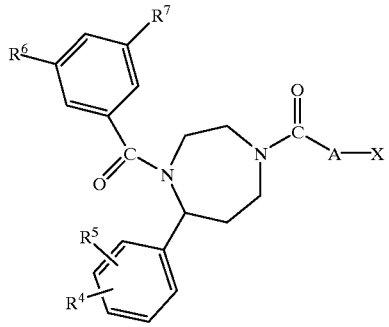

wherein $R^4$, $R^5$, $R^6$, $R^7$ and A have the above meanings and X represents a cleavable leaving group, with a compound of formula IXa:

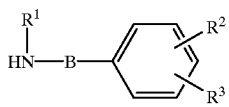

wherein $R^1$, $R^2$, $R^3$ and B have the above meanings, or e) to prepare a compound of Formula I, reacting a compound of formula X:

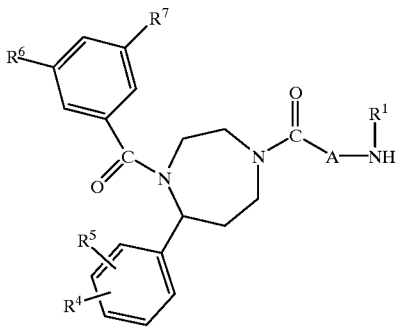

wherein $R^1$, $R^4$, $R^5$, $R^6$, $R^7$ and A have the above meanings, under conditions of reductive alkylation with a compound of formula XIa:

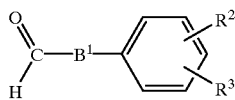

wherein $R^2$ and $R^3$ have the above meanings and $B^1$ represents a bond or an alkylene chain with 1 to 2 carbon atoms, optionally substituted by lower alkyl, or with a compound of formula XIb:

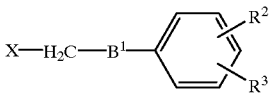

wherein $R^2$, $R^3$, $B^1$ and X have the above meanings, and optionally alkylating a resulting compound of Formula I wherein $R^1$ is hydrogen to form a compound of Formula I wherein $R^1$ is lower alkyl, or optionally converting a resulting compound of Formula I into an acid addition salt thereof or converting an acid addition salt into a free compound of Formula I.

* * * * *